(12) United States Patent
Djuranovic et al.

(10) Patent No.: US 12,274,731 B1
(45) Date of Patent: Apr. 15, 2025

(54) POLYBASIC ANTIMALARIAL AGENTS AND METHODS OF USE THEREOF

(71) Applicants: Sergej Djuranovic, St. Louis, MO (US); Slavica Pavlovic Djuranovic, St. Louis, MO (US); Jessey Lee Erath, St. Louis, MO (US)

(72) Inventors: Sergej Djuranovic, St. Louis, MO (US); Slavica Pavlovic Djuranovic, St. Louis, MO (US); Jessey Lee Erath, St. Louis, MO (US)

(73) Assignee: Washington University, St. Louis, MO (US)

( * ) Notice: Subject to any disclaimer, the term of this patent is extended or adjusted under 35 U.S.C. 154(b) by 441 days.

(21) Appl. No.: 16/509,812

(22) Filed: Jul. 12, 2019

Related U.S. Application Data

(60) Provisional application No. 62/696,868, filed on Jul. 12, 2018.

(51) Int. Cl.
*A61P 33/06* (2006.01)
*A61K 38/02* (2006.01)
*A61K 38/03* (2006.01)
*A61K 47/60* (2017.01)

(52) U.S. Cl.
CPC .............. *A61K 38/02* (2013.01); *A61K 47/60* (2017.08); *A61P 33/06* (2018.01)

(58) Field of Classification Search
CPC .......... A61K 38/02; A61K 47/60; A61P 33/06
See application file for complete search history.

(56) References Cited

U.S. PATENT DOCUMENTS

| | | | |
|---|---|---|---|
| 5,472,953 A | 12/1995 | Ekre et al. | |
| 10,285,952 B2 * | 5/2019 | Zhang .............. | G01N 33/56905 |
| 2003/0099663 A1 | 5/2003 | Fleitmann et al. | |
| 2013/0137732 A1 * | 5/2013 | Busch .................... | A01N 37/46 |
| | | | 514/358 |
| 2014/0171438 A1 | 6/2014 | Pan et al. | |
| 2014/0308317 A1 | 10/2014 | Fan et al. | |
| 2015/0098989 A1 | 4/2015 | Ferrer Montiel et al. | |

FOREIGN PATENT DOCUMENTS

| | | |
|---|---|---|
| EP | 2756852 A1 | 7/2014 |
| WO | WO 03/075912 | 9/2003 |

OTHER PUBLICATIONS

Bhadra, D., et al. Proceedings of the 2004 International Conference on MEMS, NANO and Smart Systems (ICMENS'04) (2004); 2 pages.*
Okuda, T., et al. J. Control. Release (2006), 114; 69-77.*
Flannery, E. L., et al. Nat. Rev. Microbiol. (2013), 11(12); 849-862.*
Kumar et al 2015 (Year: 2015).*
Pretzel et al 2013 (Year: 2013).*
Andrews RJ, Baber L, Moss WN. RNAStructuromeDB: A genome-wide database for RNA structural inference. Scientific Reports. 2017;7(1):1-13. doi:10.1038/s41598-017-17510-y.
Arthur LL, Chung JJ, Janakirama P, et al. Rapid generation of hypomorphic mutations. Nature Communications. 2017;8(1):1-16. doi:10.1038/ncomms14112.
Arthur LL, Djuranovic S. PolyA tracks, polybasic peptides, poly-translational hurdles. Wiley Interdiscip Rev RNA. Jun. 2018:e1486. doi:10.1002/wrna.1486.
Arthur LL, Pavlovic-Djuranovic S, Koutmou KS, Green R, Szczesny P, Djuranovic S. Translational control by lysine-encoding A-rich sequences. Science Advances. 2015;1(6):e1500154. doi:10.1126/sciadv.1500154.
Babbitt SE, Altenhofen L, Cobbold SA, et al. Plasmodium falciparum responds to amino acid starvation by entering into a hibernatory state. Proceedings of the National Academy of Sciences. 2012;109(47):E3278-E3287. doi:10.1073/pnas.1209823109.
Bannister L, Mitchell G. The ins, outs and roundabouts of malaria. Trends Parasitol. 2003;19(5):209-213. doi:10.1016/s1471-4922(03)00086-2.
Barragan A, Spillmann D, Kremsner PG, Wahlgren M, Carlson J. Plasmodium falciparum: molecular background to strain-specific rosette disruption by glycosaminoglycans and sulfated glycoconjugates. Exp Parasitol. 1999;91(2):133-143. doi:10.1006/expr.1998.4349.
Bhattacharya A, McIntosh KB, Willis IM, Warner JR. Why Dom34 stimulates growth of cells with defects of 40S ribosomal subunit biosynthesis. Mol Cell Biol. 2010;30(23):5562-5571. doi:10.1128/MCB.00618-10.
Boyle MJ, Richards JS, Gilson PR, Chai W, Beeson JG. Interactions with heparin-like molecules during erythrocyte invasion by Plasmodium falciparum merozoites. Blood. 2010;115(22):4559-4568. doi:10.1182/blood-2009-09-243725.
Brandman O, Stewart-Ornstein J, Wong D, et al. A ribosome-bound quality control complex triggers degradation of nascent peptides and signals translation stress. Cell. 2012;151(5):1042-1054. doi:10.1016/.cell.2012.10.044.
Bunnik EM, Chung D-WD, Hamilton M, et al. Polysome profiling reveals translational control of gene expression in the human malaria parasite *Plasmodium falciparum*. Genome Biol. 2013;14(11):R128. doi:10.1186/GB-2013-14-11-r128.
Caro F, Ahyong V, Betegon M, Derisi JL. Genome-wide regulatory dynamics of translation in the Plasmodium falciparum asexual blood stages. Gingeras TR, ed. eLife. 2014;3:e04106. doi:10.7554/eLife.04106.
Coulson RMR, Hall N, Ouzounis CA. Comparative Genomics of Transcriptional Control in the Human Malaria Parasite *Plasmodium falciparum*. Genome Res. 2004;14(8):1548-1554. doi:10.1101/gr.2218604.

(Continued)

*Primary Examiner* — Catherine S Hibbert

(57) ABSTRACT

Among the various aspects of the present disclosure is the provision of methods of suppressing *Plasmodium* parasite growth or infectivity or treating malaria comprising administering a polybasic antimalarial agent. The polybasic peptides and polymers provided can be used for the treatment of *Plasmodium falciparum* and other *plasmodium* species that cause human malaria.

17 Claims, 28 Drawing Sheets

Figure 1A:
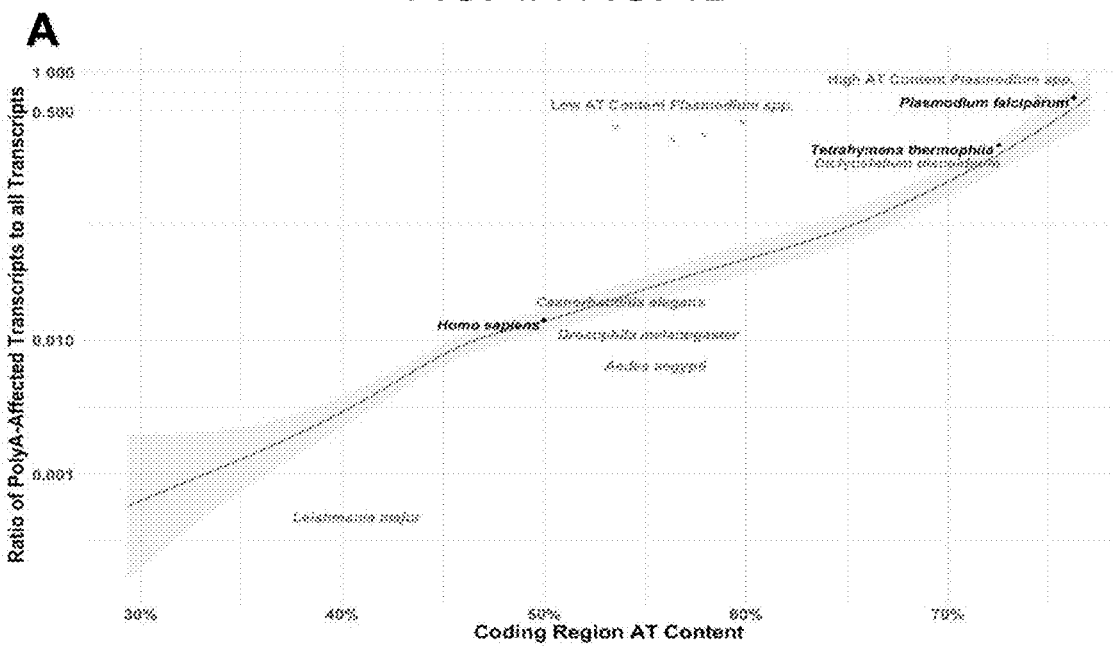

Specification includes a Sequence Listing.

(56) References Cited

OTHER PUBLICATIONS

Davies HM, Thalassinos K, Osborne AR. Expansion of Lysine-rich Repeats in Plasmodium Proteins Generates Novel Localization Sequences That Target the Periphery of the Host Erythrocyte. J Biol Chem. 2016;291(50):26188-26207. doi:10.1074/bc.M116.761213.
Doma MK, Parker R. Endonucleolytic cleavage of eukaryotic mRNAs with stalls in translation elongation. Nature. 2006;440(7083):561-564. doi:10.1038/nature04530.
Fujita H, Yamagishi M, Kida Y, Sakaguchi M. Positive charges on the translocating polypeptide chain arrest movement through the translocon. J Cell Sci. 2011;124(Pt 24):4184-4193. doi:10.1242/ics. 086850.
Garzia A, Jafarnejad SM, Meyer C, et al. The E3 ubiquitin ligase and RNA-binding protein ZNF598 orchestrates ribosome quality control of premature polyadenylated mRNAs. Nature Communications. 2017;8(1):1-10. doi:10.1038/ncomms16056.
Gerald N, Mahajan B, Kumar S. Mitosis in the human malaria parasite Plasmodium falciparum. Eukaryotic Cell. 2011;10(4):474-482. doi:10.1128/EC.00314-10.
Ghorbal M, Gorman M, MacPherson CR, Martins RM, Scherf A, Lopez-Rubio J-J. Genome editing in the human malaria parasite Plasmodium falciparum using the CRISPR-Cas9 system. Nat Biotechnol. 2014;32(8):819-821. doi:10.1038/nbt.2925.
Glöckner G, Rosenthal A, Valentin K. The structure and gene repertoire of an ancient red algal plastid genome. J Mol Evol. 2000;51(4):382-390. doi:10.1007/s002390010101.
Guler JL, Freeman DL, Ahyong V, et al. Asexual Populations of the Human Malaria Parasite, Plasmodium falciparum, Use a Two-Step Genomic Strategy to Acquire Accurate, Beneficial DNA Amplifications. PLOS Pathogens. 2013;9(5):e1003375. doi:10.1371/journal.ppat. 1003375.
Guydosh NR, Green R. Translation of poly(A) tails leads to precise mRNA cleavage. RNA. 2017;23(5):749-761. doi:10.1261/ma.060418. 116.
Habich M, Djuranovic S, Szczesny P. PATACSDB—the database of polyA translational attenuators in coding sequences. PeerJ Comput Sci. 2016;2:e45. doi:10.7717/peeri-cs.45.
Hamilton WL, Claessens A, Otto TD, et al. Extreme mutation bias and high AT content in Plasmodium falciparum. Nucleic Acids Res. 2017;45(4):1889-1901. doi:10.1093/nar/gkw1259.
Hancock JF, Paterson H, Marshall CJ. A polybasic domain or palmitoylation is required in addition to the CAAX motif to localize p21ras to the plasma membrane. Cell. 1990;63(1):133-139. doi:10. 1016/0092-8674(90)90294-0.
Ingolia NT, Brar GA, Stern-Ginossar N, et al. Ribosome profiling reveals pervasive translation outside of annotated protein-coding genes. Cell Rep. 2014;8(5):1365-1379. doi:10.1016/j.celrep.2014. 07.045.
Ito-Harashima S, Kuroha K, Tatematsu T, Inada T. Translation of the poly(A) tail plays crucial roles in nonstop mRNA surveillance via translation repression and protein destabilization by proteasome in yeast. Genes Dev. 2007;21(5):519-524. doi:10.1101/gad.1490207.
Juszkiewicz S, Hegde RS. Initiation of Quality Control during Poly(A) Translation Requires Site-Specific Ribosome Ubiquitination. Mol Cell. 2017;65(4):743-750.e4. doi:10.1016/j.molcel.2016. 11.039.
Kobayashi K, Takano R, Takemae H, et al. Analyses of Interactions Between Heparin and the Apical Surface Proteins of Plasmodium falciparum. Sci Rep. 2013;3(1):3178. doi:10.1038/srep03178.
Koutmou KS, Schuller AP, Brunelle JL, Radhakrishnan A, Djuranovic S, Green R. Ribosomes slide on lysine-encoding homopolymeric A stretches. Elife. 2015;4. doi:10.7554/eLife.05534.
Kuroha K, Akamatsu M, Dimitrova L, et al. Receptor for activated C kinase 1 stimulates nascent polypeptide-dependent translation arrest. EMBO Rep. 2010;11(12):956-961. doi:10.1038/embor.2010. 169.
Lang W-H, Calloni G, Vabulas RM. Polylysine is a Proteostasis Network-Engaging Structural Determinant. J Proteome Res. 2018;17(5):1967-1977. doi:10.1021/acs.iproteome.8b00108.

Leitgeb AM, Blomqvist K, Cho-Ngwa F, et al. Low anticoagulant heparin disrupts Plasmodium falciparum rosettes in fresh clinical isolates. Am J Trop Med Hyg. 2011;84(3):390-396. doi:10.4269/ ajtmh.2011.10-0256.
Lu XM, Batugedara G, Lee M, Prudhomme J, Bunnik EM, Le Roch KG. Nascent RNA sequencing reveals mechanisms of gene regulation in the human malaria parasite Plasmodium falciparum. Nucleic Acids Res. 2017;45(13):7825-7840. doi:10.1093/nar/gkx464.
Lutgen P. Arginine, a deadly weapon against gametocytes. | MalariaWorld. Malaria World. https://malariaworld.org/blog/arginine-deadly-weapon-against-gametocytes. Published Jul. 5, 2015. Accessed Mar. 10, 2020.
Marques J, Moles E, Urban P, et al. Application of heparin as a dual agent with antimalarial and liposome targeting activities toward Plasmodium-infected red blood cells. Nanomedicine. 2014;10(8):1719-1728. doi:10.1016/j.nano.2014.06.002.
Matsuo Y, Ikeuchi K, Saeki Y, et al. Ubiquitination of stalled ribosome triggers ribosome-associated quality control. Nature Communications. 2017;8(1):1-14. doi:10.1038/s41467-017-00188-1.
Michel AM, Fox G, M. Kiran A, et al. GWIPS-viz: development of a ribo-seq genome browser. Nucleic Acids Res. 2014;42(Database issue):D859-D864. doi:10.1093/nar/gkt1035.
Nasamu AS, Glushakova S, Russo I, et al. Plasmepsins IX and X are essential and druggable mediators of malaria parasite egress and invasion. Science. 2017;358(6362):518-522. doi:10.1126/science. aan1478.
Pérez-Picaso L, Velasco-Bejarano B, Aguilar-Guadarrama AB, Argotte-Ramos R, Rios MY. Antimalarial activity of ultra-short peptides. Molecules. 2009;14(12):5103-5114. doi:10.3390/molecules14125103.
Romero LC, Nguyen TV, Deville B, Ogunjumo O, James AA. The MB2 gene family of Plasmodium species has a unique combination of S1 and GTP-binding domains. BMC Bioinformatics. 2004;5:83. doi:10.1186/1471-2105-5-83.
Saul A, Battistutta D. Codon usage in Plasmodium falciparum. Mol Biochem Parasitol. 1988;27(1):35-42. doi:10.1016/0166-6851(88)90022-9.
Sundaramoorthy E, Leonard M, Mak R, Liao J, Fulzele A, Bennett EJ. ZNF598 and RACK1 Regulate Mammalian Ribosome-Associated Quality Control Function by Mediating Regulatory 40S Ribosomal Ubiquitylation. Mol Cell. 2017;65(4):751-760.e4. doi:10. 1016/.molcel.2016.12.026.
Szafranski K, Lehmann R, Parra G, Guigo R, Glöckner G. Gene organization features in A/T-rich organisms. J Mol Evol. 2005;60(1):90-98. doi:10.1007/s00239-004-0201-2.
Tsuboi T, Kuroha K, Kudo K, et al. Dom34:hbs1 plays a general role in quality-control systems by dissociation of a stalled ribosome at the 3' end of aberrant mRNA. Mol Cell. 2012;46(4):518-529. doi:10.1016/i.molcel.2012.03.013.
Vogt AM, Pettersson F, Moll K, et al. Release of Sequestered Malaria Parasites upon Injection of a Glycosaminoglycan. PLOS Pathogens. 2006;2(9):e100. doi:10.1371/journal.ppat.0020100.
Wolf AS, Grayhack EJ. ASC1, homolog of human RACK1, prevents frameshifting in yeast by ribosomes stalled at CGA codon repeats. RNA. 2015;21(5):935-945. doi:10.1261/ma.049080.114.
Wong W, Bai X, Brown A, et al. Cryo-EM structure of the Plasmodium falciparum 80S ribosome bound to the anti-protozoan drug emetine. Kühlbrandt W, ed. eLife. 2014;3:e03080. doi:10.7554/ eLife.03080.
Zheng L, Pan Y, Feng Y, Cui L, Cao Y. L-Arginine supplementation in mice enhances NO production in spleen cells and inhibits Plasmodium yoelii transmission in mosquitoes. Parasit Vectors. 2015;8. doi:10.1186/s13071-015-0940-0.
ClinicalTrials.gov. Identifier: NCT02078648, Safety and Efficacy Study of SL-701, a Glioma-Associated Antigen Vaccine to Treat Recurrent Glioblastoma Multiforme—Full Text View—ClinicalTrials. gov. ClinicalTrials.gov. First posted 2014. https://clinicaltrials.gov/ ct2/show/NCT02078648. Accessed Jun. 30, 2022. 10 pages.
Gardner MJ, Hall N, Fung E, et al. Genome sequence of the human malaria parasite Plasmodium falciparum. Nature. 2002;419(6906):498-511. doi:10.1038/nature01097.
Johnston TP, Kuchimanchi KR, Alur H, Chittchang M, Mitra AK. Inducing a change in the pharmacokinetics and biodistribution of

(56) References Cited

OTHER PUBLICATIONS poly-l-lysine in rats by complexation with heparin. Journal of Pharmacy and Pharmacology. 2003;55(8):1083-1090. doi:10.1211/0022357021530.

Sorber K, Dimon MT, Derisi JL. RNA-Seq analysis of splicing in Plasmodium falciparum uncovers new splice junctions, alternative splicing and splicing of antisense transcripts. Nucleic Acids Res. 2011;39(9):3820-3835. doi:10.1093/nar/gkq1223.

Sun M, Li W, Blomqvist K, et al. Dynamical features of the Plasmodium falciparum ribosome during translation. Nucleic Acids Res. 2015;43(21):10515-10524. doi:10.1093/nar/gkv991.

Weinberg JB, Lopansri BK, Mwaikambo E, Granger DL. Arginine, nitric oxide, carbon monoxide, and endothelial function in severe malaria. Curr Opin Infect Dis. 2008;21(5):468-475. doi:10.1097/QCO.0b013e32830ef5cf.

Zhang M, Wang C, Otto TD, et al. Uncovering the essential genes of the human malaria parasite *Plasmodium falciparum* by saturation mutagenesis. Science. 2018;360(6388). doi:10.1126/science.aap7847.

\* cited by examiner

***P. falciparum* Absolute Codon Counts ( log₁₀ )**

FIG. 13A-FIG. 13B
A
*P. falciparum* 80S Ribosome
(3JBO)
*H. sapiens* 80S Ribosome
(3JAG)
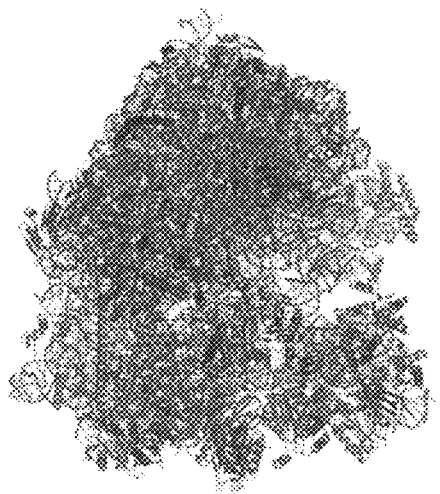
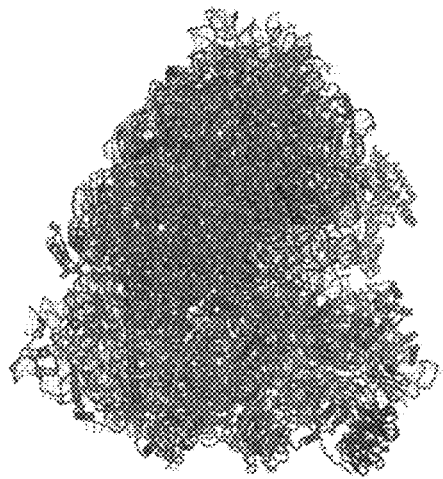
B
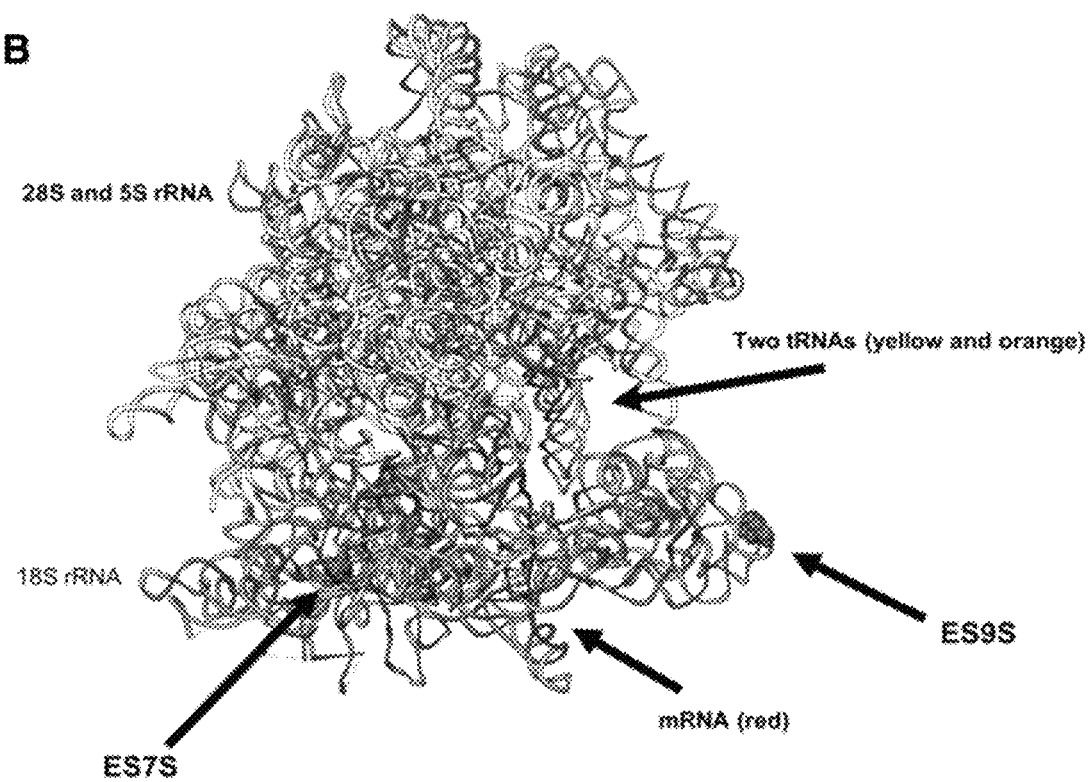

| | Heparine | PEG-polyLys 50 | polyLys 50 |
|---|---|---|---|
| LogIC50 | 30.02 | 9.419 | 25.39 |

PEG-Poly (L) Lysine
22 PEG moieties
50 (L) Lysine residues

FIG. 24

| Plasmodium species | Seq ≥ 9Lys |
|---|---|
| Plasmodium cynomolgi | 22 |
| Plasmodium chabaudi | 27 |
| Plasmodium berghei | 40 |
| Plasmodium vivax | 74 |
| Plasmodium knowlesi | 91 |
| Plasmodium yoelii YM | 130 |
| Plasmodium falciparum 3D7/IT | 140 |

PKL-50 poly(L) lysine 50 residues
$PKLC_{50}$-b-$PEG_{1K}$-b-$PKLC_{50}$ polymer with 2x 50poly(L)Lys residues and 22 PEG moieties
$PKLC_{10}$-b-$PEG_{5k}$-b-$PKLC_{10}$ polymer with 2x 10poly(L)Lys residues and 113 PEG moieties
Poly epsilon L-Lysine (mix of 20-200 residues)

$PKLC_x$-b-$PEG_n$-b-$PKLC_x$

POLYBASIC ANTIMALARIAL AGENTS AND METHODS OF USE THEREOF

CROSS-REFERENCE TO RELATED APPLICATIONS

This application claims priority from U.S. Provisional Application Ser. No. 62/696,868 filed on 12 Jul. 2018, which is incorporated herein by reference in its entirety.

STATEMENT REGARDING FEDERALLY SPONSORED RESEARCH OR DEVELOPMENT

Not applicable.

MATERIAL INCORPORATED-BY-REFERENCE

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The present disclosure generally relates to antimalarial compositions and uses thereof.

SUMMARY OF THE INVENTION

Among the various aspects of the present disclosure is the provision of polybasic antimalarial agents and methods of use thereof.

An aspect of the present disclosure provides for a method of suppressing or preventing *Plasmodium* parasite growth or infectivity in a subject comprising: administering a therapeutically effective amount of a polybasic antimalarial agent comprising a polybasic compound, a polybasic protein, a polybasic peptide, or a polybasic polymer to a *Plasmodium* parasite cell in an amount sufficient to suppress the *Plasmodium* parasite growth or infectivity.

In some embodiments, the therapeutically effective amount of a polybasic antimalarial agent is an amount sufficient to inhibit cellular adhesion of the *Plasmodium* parasite or inhibit interaction of the *Plasmodium* parasite with an erythrocyte.

In some embodiments, the polybasic antimalarial agent has a net positive charge.

In some embodiments, the subject is a human or a mosquito.

In some embodiments, the subject has malaria, is suspected of having malaria, or is at risk for contracting malaria.

In some embodiments, the polybasic antimalarial agent comprises: (i) one or more of a lysine, an ornithine, an arginine, or a histidine; or (ii) one or more of a poly-lysine repeat, a poly-ornithine repeat, a poly-arginine repeat, or a poly-histidine repeat.

In some embodiments, the polybasic antimalarial agent is conjugated to a PEG, a dextran, a rhodamine dextran, or a dendrimer.

In some embodiments, the polybasic protein or polybasic polymer has a molecular weight between about 1 kDa and about 15 kDa or has a distribution of molecular weights having an average molecular weight between about 1 kDa and about 15 kDa; In some embodiments, the polybasic peptide comprises greater than 10 polybasic amino acids or between about 10 polybasic amino acids and about 50 amino acids; or the polybasic polymer comprises greater than about 50 polybasic amino acids.

In some embodiments, the *Plasmodium* parasite is selected from the group consisting of *Plasmodium falciparum, Plasmodium yoelii, Plasmodium knowlesi, Plasmodium vivax, Plasmodium berghei, Plasmodium chabaudi,* and *Plasmodium cynomolgi.*

In some embodiments, the polybasic peptide has an $IC_{50}$ of less than about 30 µg/ml, less than about 20 µg/ml, or less than about 10 µg/ml.

In some embodiments, the polybasic antimalarial agent competes with endogenous poly-lysine and polybasic proteins for cell binding or the polybasic antimalarial agent blocks *Plasmodium* adhesion to cells.

In some embodiments, the polybasic antimalarial agent substantially targets malaria-infected erythrocytes and do not detectably bind to uninfected cells.

Another aspect of the present disclosure provides for a method of treating or preventing malaria in a subject comprising: administering a therapeutically effective amount of a polybasic antimalarial agent comprising a polybasic compound, polybasic protein, polybasic peptide, or polybasic polymer.

In some embodiments, the therapeutically effective amount of a polybasic antimalarial agent is an amount sufficient to inhibit cellular adhesion of a *Plasmodium* parasite or inhibit interaction of the *Plasmodium* parasite with an erythrocyte.

In some embodiments, the polybasic antimalarial agent has a net positive charge.

In some embodiments, the subject is a human or a mosquito.

In some embodiments, the subject has malaria, is suspected of having malaria, or is at risk for contracting malaria.

In some embodiments, the polybasic antimalarial agent comprises: (i) one or more of a lysine, an ornithine, an arginine, or a histidine; or (ii) one or more of a poly-lysine repeat, a poly-ornithine repeat, a poly-arginine repeat, or a poly-histidine repeat.

In some embodiments, the polybasic antimalarial agent is conjugated to a PEG, a dextran, a rhodamine dextran, or a dendrimer.

In some embodiments, the polybasic protein or the polybasic polymer has a molecular weight between about 1 kDa and about 15 kDa or has a distribution of molecular weights having an average molecular weight between about 1 kDa and about 15 kDa; the polybasic peptide comprises greater than 10 polybasic amino acids or between about 10 polybasic amino acids and about 50 amino acids; or the polybasic polymer comprises greater than about 50 polybasic amino acids.

In some embodiments, the *Plasmodium* parasite is selected from the group consisting of *Plasmodium falciparum, Plasmodium yoelii, Plasmodium knowlesi, Plasmodium vivax, Plasmodium berghei, Plasmodium chabaudi,* and *Plasmodium cynomolgi.*

In some embodiments, the polybasic antimalarial agent competes with endogenous poly-lysine and polybasic proteins for cell binding or the polybasic antimalarial agent blocks *Plasmodium* adhesion to cells.

Another aspect of the present disclosure provides for a net comprising a polybasic antimalarial agent comprising one or more of a polybasic compound, polybasic protein, polybasic peptide, or polybasic polymer, wherein the polybasic antimalarial agent has the ability to treat or prevent malaria in a mosquito.

Other objects and features will be in part apparent and in part pointed out hereinafter.

DESCRIPTION OF THE DRAWINGS

Those of skill in the art will understand that the drawings, described below, are for illustrative purposes only. The drawings are not intended to limit the scope of the present teachings in any way.

FIG. 1A-FIG. 1C. (A) A plot of 152 species representing a comparison of the ratio of polyA-affected transcripts (over a total number of transcripts) to the AT content of coding region for each organism. Pertinent organisms are depicted in black, while other model organisms of interest are displayed in gray, including a position of various *Plasmodium* spp. (B) Transcript counts for genes with 6 to 36 consecutive adenosines for *H. sapiens, T. thermophila*, and *P. falciparum. H. sapiens* and *T. thermophila* are limited to a single transcript at length of ≤17As. The longest *P. falciparum* transcript reaches maximal 65As, with multiple transcripts of ≤36As. (C) Violin plot of lysine codon usage distribution in tracks of four lysine residues for 152 organisms. *H. sapiens* (circle), *T. thermophila* (triangle), and *P. falciparum* (square).

FIG. 2A-FIG. 2D. (A) Box and whisker plots depicting the distribution of mean folding energy values (kcal/mol; measures the stability of RNA structure) calculated for each coding sequence from *H. sapiens, T. thermophile*, and *P. falciparum*, resulting from a scanning window analysis. Center lines show the medians; box limits indicate the 25th and 75th percentiles; whiskers extend 1.5 times the interquartile range from the 25th and 75th percentiles; outliers are represented by dots; numbers below plots are the number of coding sequences for each species. (B) Box and whisker plots showing the distribution of mean z-score values (e.g., measures degree to which native sequence RNA structure is stable vs. random) calculated for each coding sequence from *H. sapiens, T. thermophila*, and *P. falciparum*, resulting from a scanning window analysis. Plots are structured as in (A). Occupancy of elongating ribosomes (mapped to A-site) around the start of polyA segments in human (C) and *P. falciparum* (D). In both cases, to avoid inclusion of sparsely mapped segments, regions with average occupancy below the mean for the whole dataset were excluded. In the case of *P. falciparum*, gene segments with polyA tracks shorter than 22 nucleotides were taken into account.

FIG. 3A-FIG. 3D. (A) mRNA abundance of reporter constructs (+polyA36) by qRT-PCR relative to their counterpart lacking polyA stretches (−polyA36) in *H. sapiens, T. thermophila*, and *P. falciparum* cells. Data represent three biological replicates with a standard deviation. (B) Expression of reporter constructs in *H. sapiens, T. thermophila*, and *P. falciparum* followed by western blot analysis with αHA or αGFP antisera. Samples from two integrated clones for the −polyA36 control (−A) and the +polyA36 reporter (+A) are shown for *T. thermophila*. αβ-actin, α-acetylated alpha-tubulin (ATU) and αhDHFR are used as loading controls for western blot analysis from *H. sapiens, T. thermophila* and *P. falciparum* cells, respectively. (C) Images from live fluorescence microscopy of *P. falciparum* expression of reporter constructs with (+PolyA36) and without (−PolyA36) polyA tracks as well as parent (non-transfected) line, 2.5 μm scale bar. (D) Quantification of protein amounts for Thioredoxin-2HA-NanoLuciferase (Trx-2HA-NLuc) reporter without (−polyA36) and with 36 adenosine stretch (+polyA36) expressed in *P. falciparum* cells. Western blot analysis of Trx-2HA-NLuc reporter (see e.g., FIG. 5) and luminescence measurements were normalized to hDHFR or cell number, respectively. Luminescence data represents mean value of three biological replicates with standard deviation.

FIG. 4A-FIG. 4D. (A) Relative mRNA enrichment for *P. falciparum* GAPDH (PF3D7_1462800), HSP70 (PF3D7_0818900), Pelo (PF3D7_0722100) and palmitoyl-transferase (DHHC8; PF3D7_1321400) transcripts after 48 hours isoleucine (Ile) starvation of the *P. falciparum* cells. DHHC8 transcript codes for five consecutive lie-residues. Levels of each transcript are normalized to total ribosome levels and represented as a ratio of transcript levels under Ile starvation (−Ile) over the control conditions (+Ile). (B) Increased levels of *P. falciparum* HSP70 and Pelo proteins after 48 hours of Ile starvation. Western blot analysis of Ile starved (−Ile), and control (+Ile) sample are normalized to PfHAD1 (PF3D7_1033400) levels. HA-tagged *P. falciparum* Pelo protein was CRISPR/Cas9 engineered and detected using mouse HA-antibody. The molecular weight of each protein is indicated. (C) Polypeptide exit channel from *Plasmodium* ribosome (PDB: 3j79) has relatively short fragments (up to 3 Angstroms) of the relatively hydrophobic lining of the tunnel. Two major patches observed in other organisms are rRNA flanked (upper panel, interacting molecules with atoms shown) and L22 and L4 flanked (lower panel). (D) *P. falciparum* growth assay in the presence of different compounds and amino acid polymers. Data represent endpoint parasitemia after 72-hour treatment with the indicated compound. Results are normalized to non-treated cultures (control) and presented as a percentage of control samples. Average value from three biological replicates is reported with standard deviation.

FIG. 5. Percentage of genes with ≥12 consecutive adenosine nucleotides for each organism. Number of genes was calculated as percentage of total number of genes with ≥12 consecutive adenosine nucleotides over total number of genes for each organism.

FIG. 6. Absolute codon usage counts in *P. falciparum* as on log 10 scale. Lysine AAA and asparagine (AAU) codons show extreme bias over their cognate codons.

FIG. 7. Occupancy of elongating ribosomes (mapped to A-site) around start of polyA segment in *Plasmodium* at different life stages. In all cases, to avoid inclusion of sparsely mapped segments, regions with average occupancy below the mean were excluded. Gene with segments shorter than 22 adenosine nucleotides were taken into account.

FIG. 8. Occupancy around polyA segment length (summarized across all life stages) grouped by polyA segment length (genes with 12-68 adenosine nucleotides are shown).

FIG. 9. Occupancy of elongating ribosomes (mapped to A-site) around start of polyA segment in *Plasmodium* at different life stages. To avoid inclusion of sparsely mapped segments, regions with average occupancy below the mean for the particular dataset were excluded. Genes with segments shorter than 22 adenosine nucleotides were taken into account. Data were normalized by dividing by a mean occupancy of a randomly selected gene segments equally numbered as polyA set from the same dataset.

FIG. 10. Time course mRNA expression analysis of three genes (PF3D7_1464200, PF3D7_0615500, PF3D7_11080000) containing polyA stretches of varying lengths (largest: 20, 21, and 31 adenosines respectively) normalized to GAPDH (PF3D7_1462800) starting with highly synchronized rings at time zero. 2−ΔΔCt values represent mRNA abundance enrichment of genes with polyA stretches over PfGAPDH mRNA levels.

Figure 11:
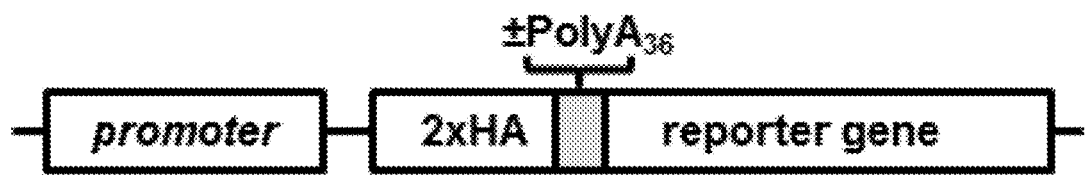

FIG. 11. Generalized scheme of reporter constructs used for expression in *H. sapiens, T. thermophila*, and *P. falciparum*.

Figure 12A:
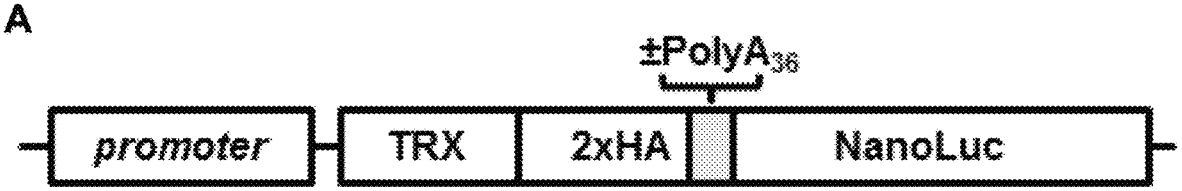
Figure 12B:
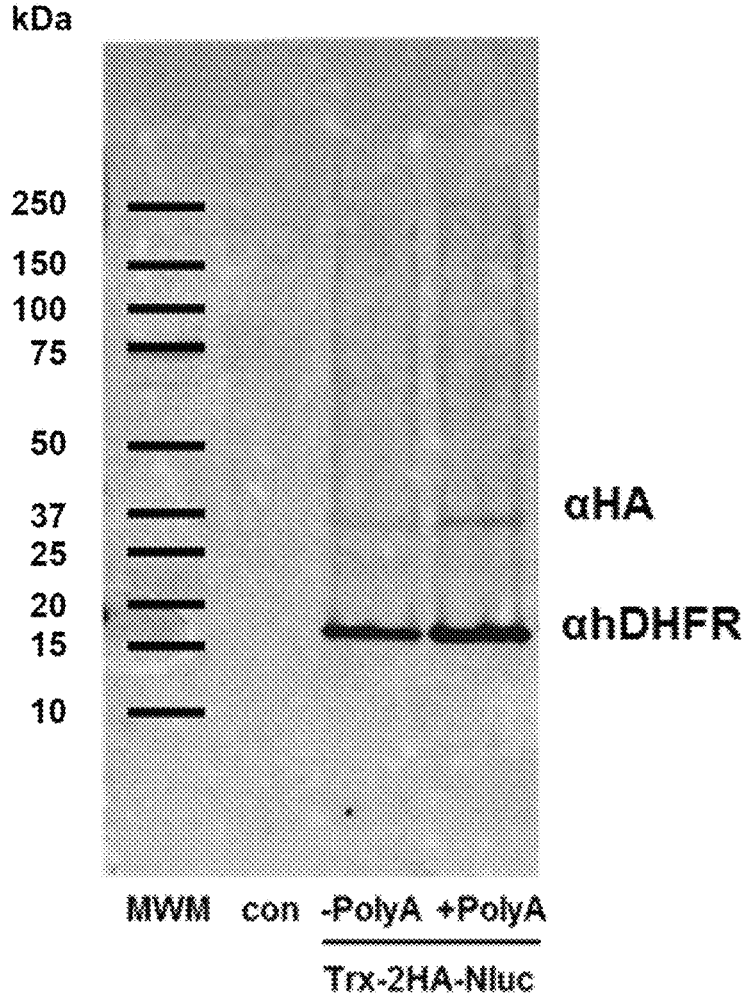

FIG. 12A-FIG. 12B. (A) Generalized schematic of Thioredoxin fusion NanoLuc reporter construct used for episomal expression in *P. falciparum* cells (Trx-2HA-Nluc). (B) Western blot analysis of Trx-2HA-Nluc reporter expression in *P. falciparum* without (−polyA36) and with 36 adenosine stretch (+polyA36). Human DHFR (hDHFR) expressed from the same plasmid is used as loading and transfection control. Untransfected *P. falciparum* control cells (con) and Biorad Precision Plus Protein™ molecular weight markers (MWM) are indicated.

FIG. 13A-FIG. 13B. (A) Structure of *P. falciparum* (PDB code: 3JBO) and *H. sapiens* (PDB code: 3JAG) ribosomes with receptor for activated kinase C (RACK1) in magenta, previously shown to be absent from *Plasmodium* ribosomes (60S in green, 40S in cyan). (B) Model of *P. falciparum* ribosome displaying small subunit ribosomal RNA sequence extensions (28S and 5S rRNAs in gray, 18S rRNA in cyan, tRNAs in yellow and orange, mRNA in red, extended sequences ES7S and ES9S in magenta). The ES7S and ES9S regions distinguish *P. falciparum* from other organisms. ES7S is located next to the binding pocket for ribosome GTPases and is adjacent to ribosome GTPase center.

Figure 14:
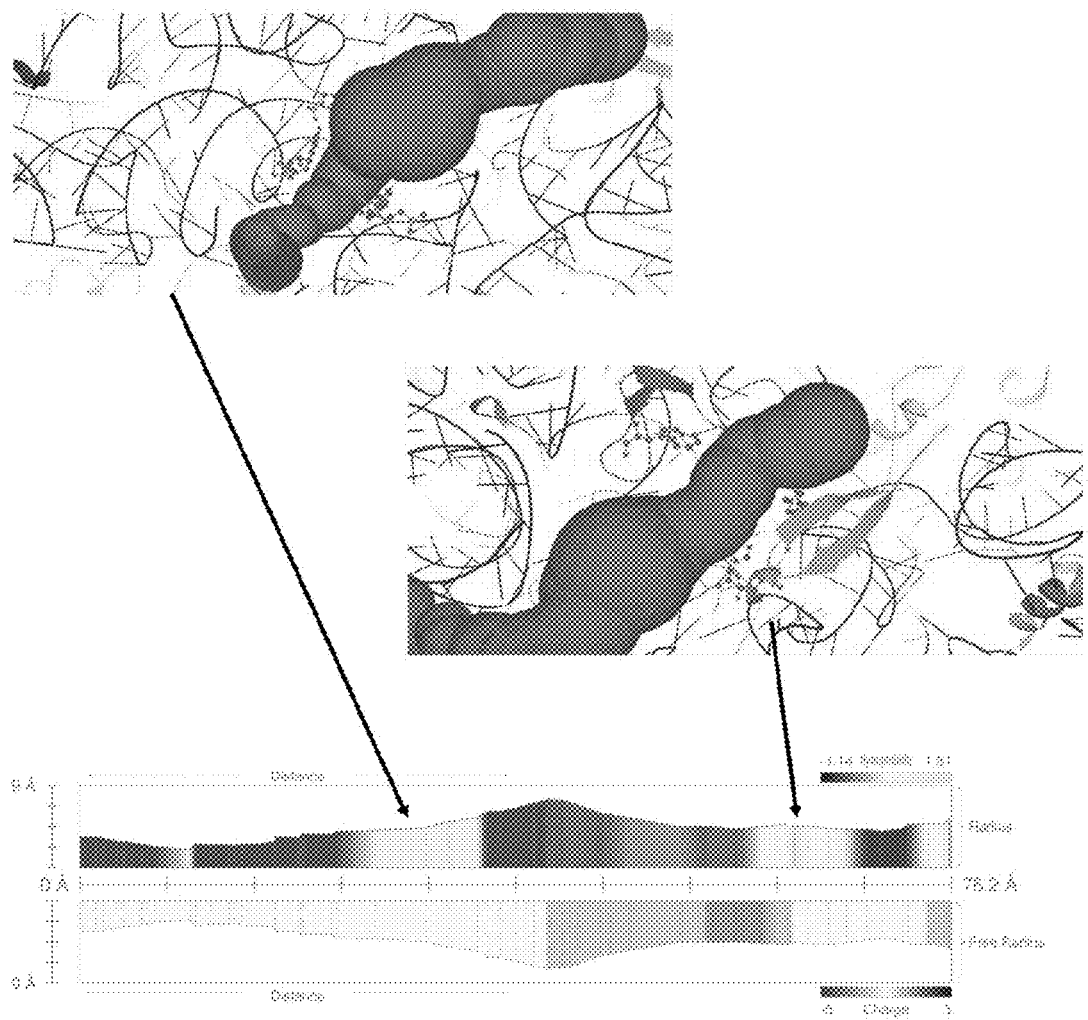

FIG. 14. Polypeptide exit channel from human ribosome (PDB: 6d90) has two long fragments (over 10 Angstroms) of relatively hydrophobic lining of the tunnel. Two major hydrophobic patches observed in other organisms are rRNA flanked (upper panel, interacting molecules have atoms shown) and L22 and L4 flanked (lower panel).

Figure 15:
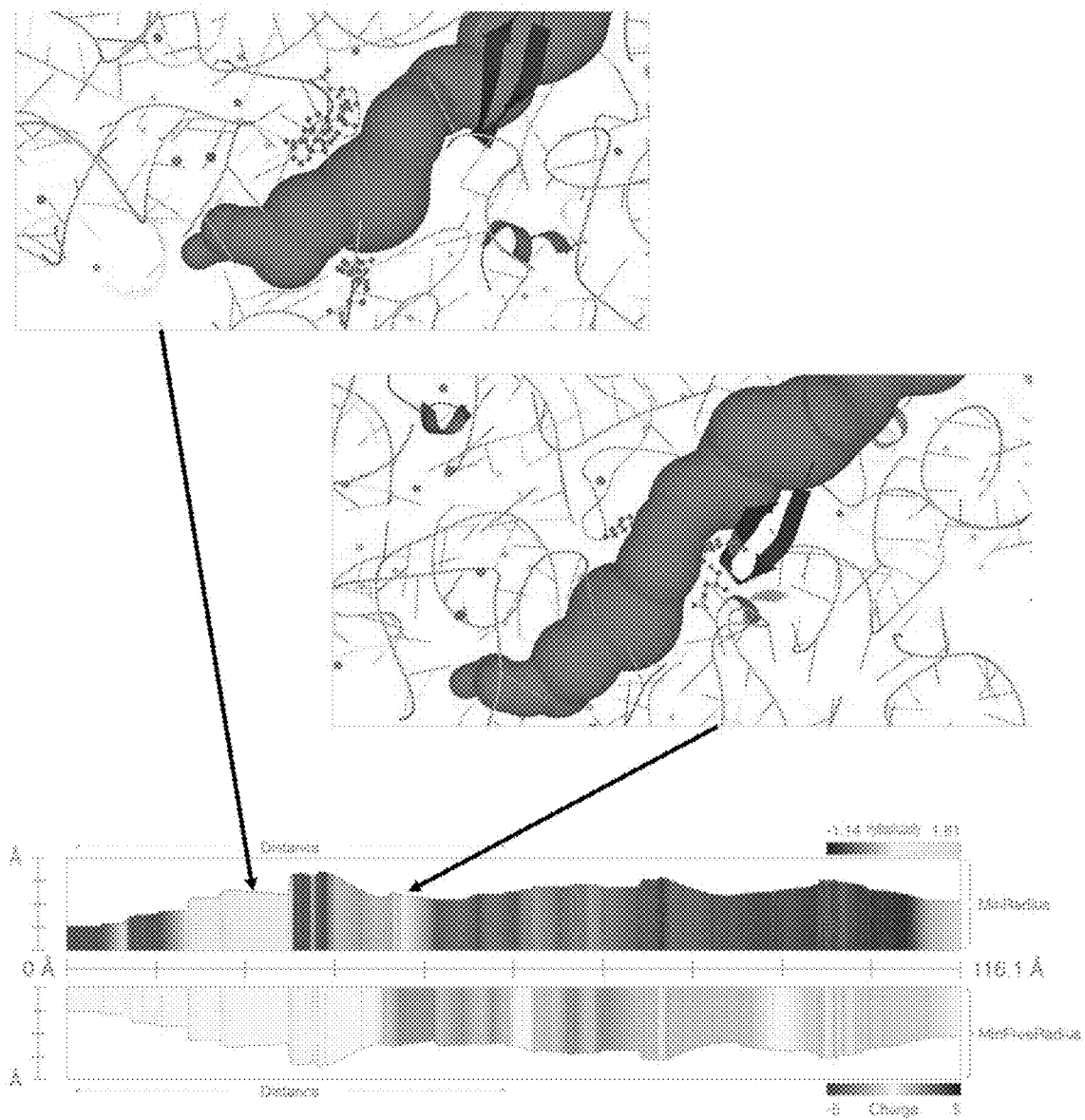

FIG. 15. Polypeptide exit channel from *Haloarcula marismortui* ribosome (PDB: 1jj2) has one long fragment (over 10 Angstroms) of relatively hydrophobic lining of the tunnel. Two major hydrophobic patches observed in other organisms are rRNA flanked (upper panel, interacting molecules have atoms shown) and L22 and L4 flanked (lower panel).

Figure 16:
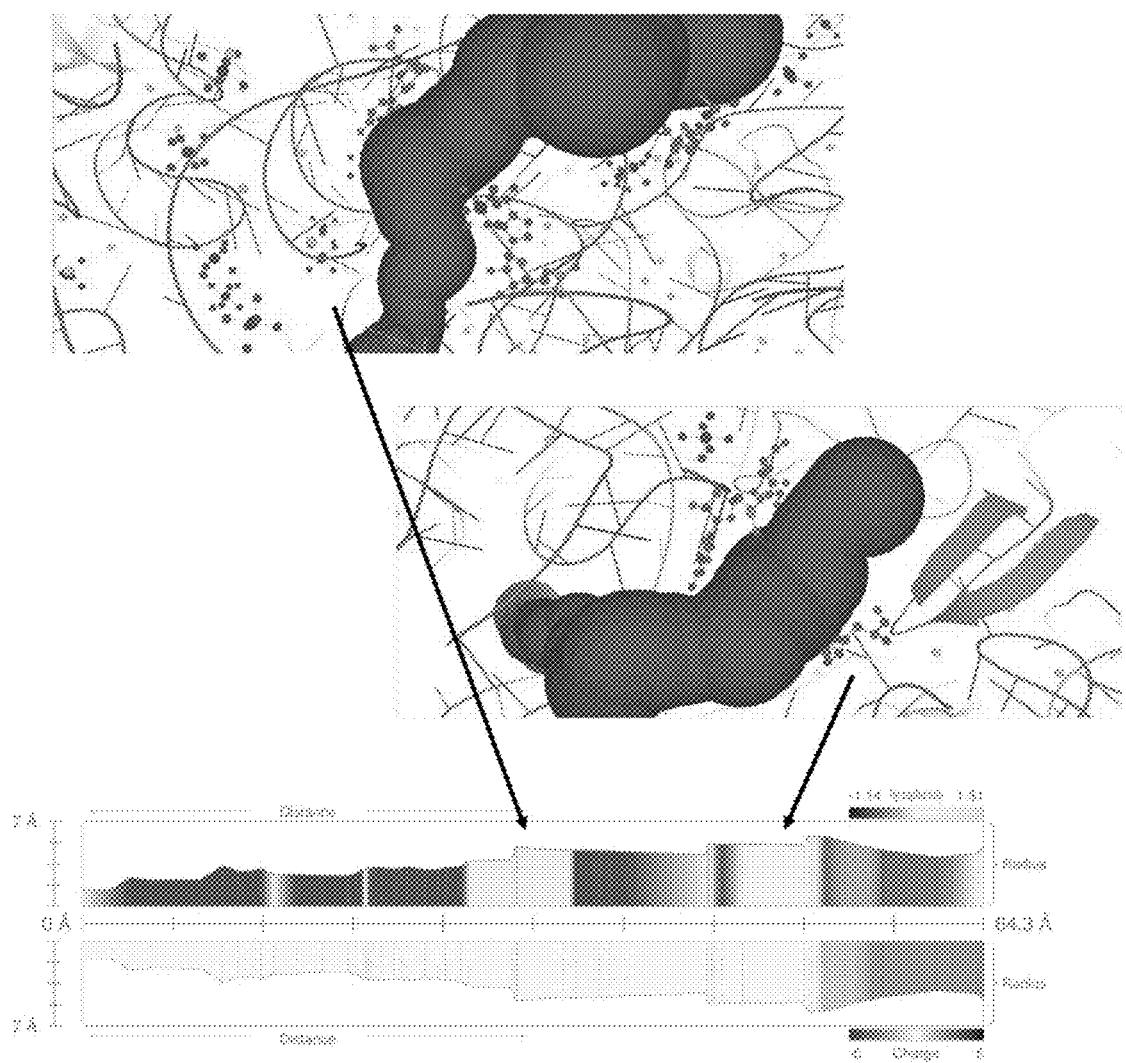

FIG. 16. Polypeptide exit channel from yeast ribosome (PDB: 5fci) has two long fragments (over 10 Angstroms) of relatively hydrophobic lining of the tunnel. Two major hydrophobic patches observed in other organisms are rRNA flanked (upper panel, interacting molecules have atoms shown) and L22 and L4 flanked (lower panel).

Figures 17A, 17B, 17C:
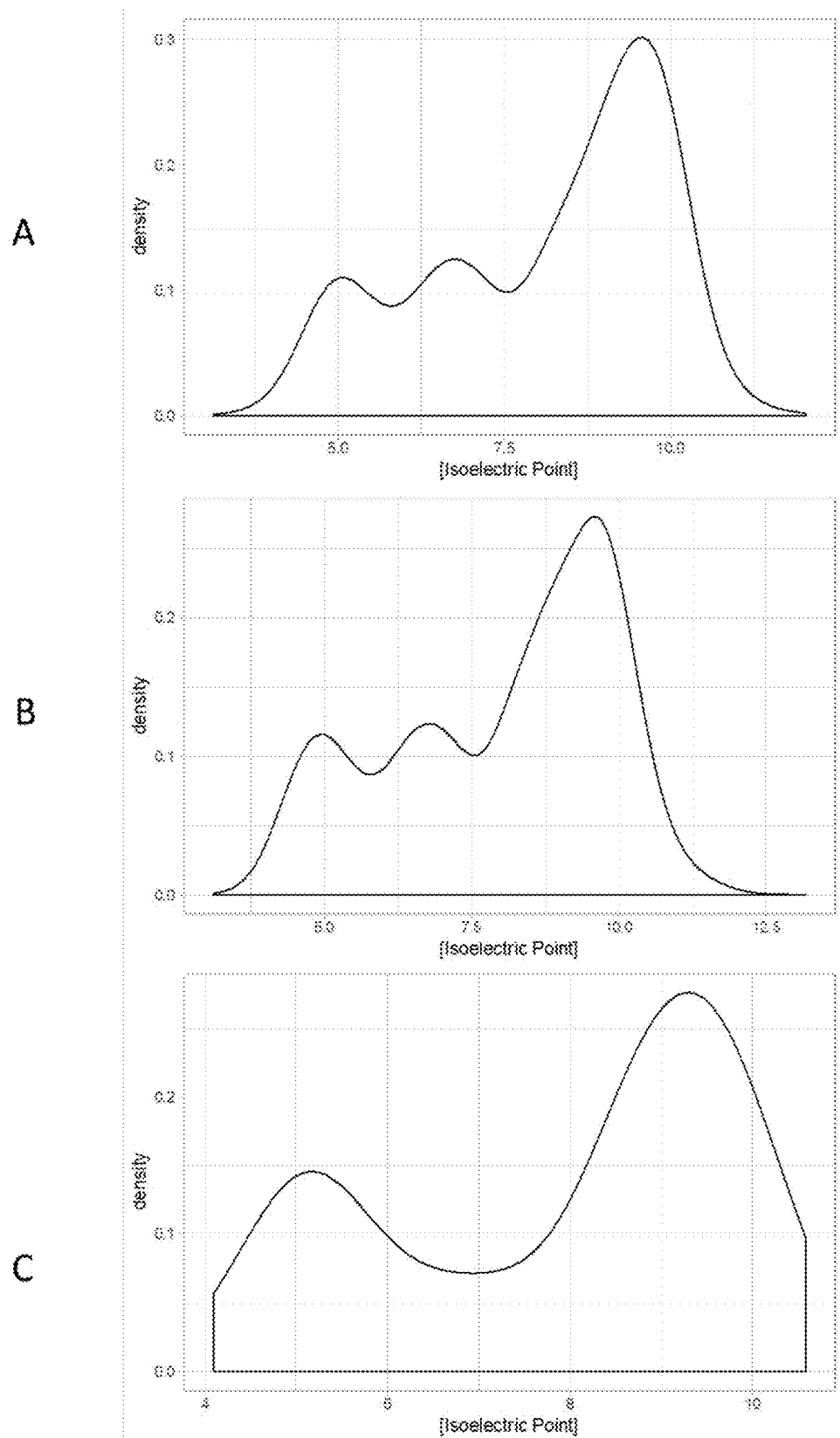

FIG. 17A-FIG. 17C. Comparison of density plots of isoelectric points of proteins encoded by (A) polyA-carrying genes in *P. falciparum* (3416 in total), (B) all *P. falciparum* proteins (5801 in total) and (C) exported proteins. All distributions do not differ significantly (p-value of Kolmogorov-Smirnov test for comparisons: A-B 0.12, A-C 0.06, B-C 0.23).

Figure 18A:
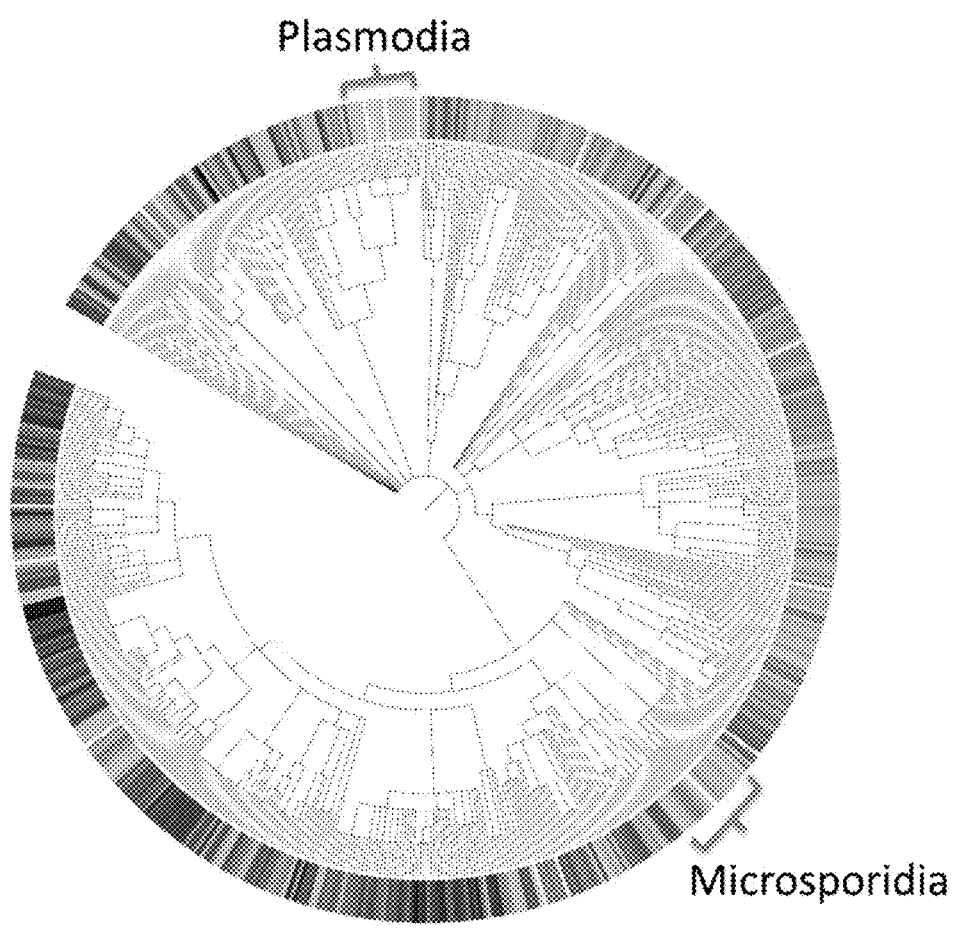
Figure 18B:
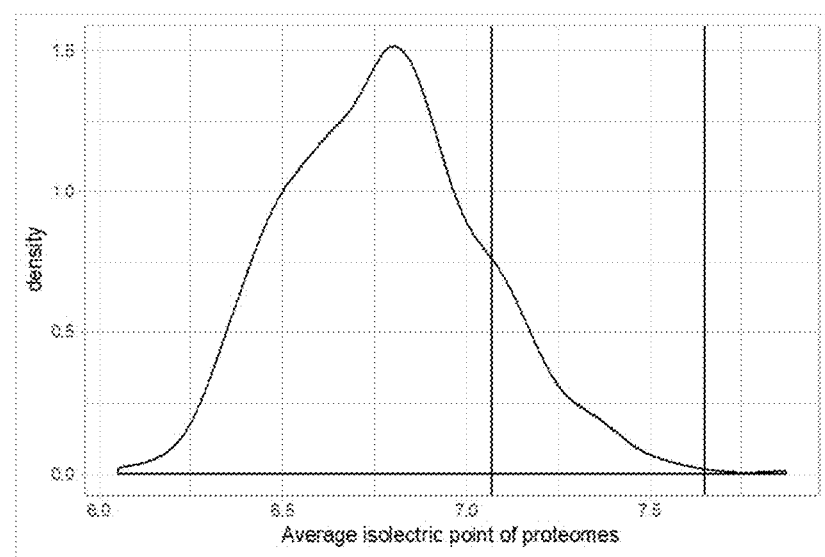

FIG. 18A-FIG. 18B (A) Distribution of average isoelectric point mapped onto taxonomic tree of eukaryotes. Plasmodia and certain Microsporidia are the only two taxonomic groups consistently having high mean pI of proteomes. (B) Density plot of the values from above plot. Range in which fit all *Plasmodium* species marked with vertical lines.

Figure 19:
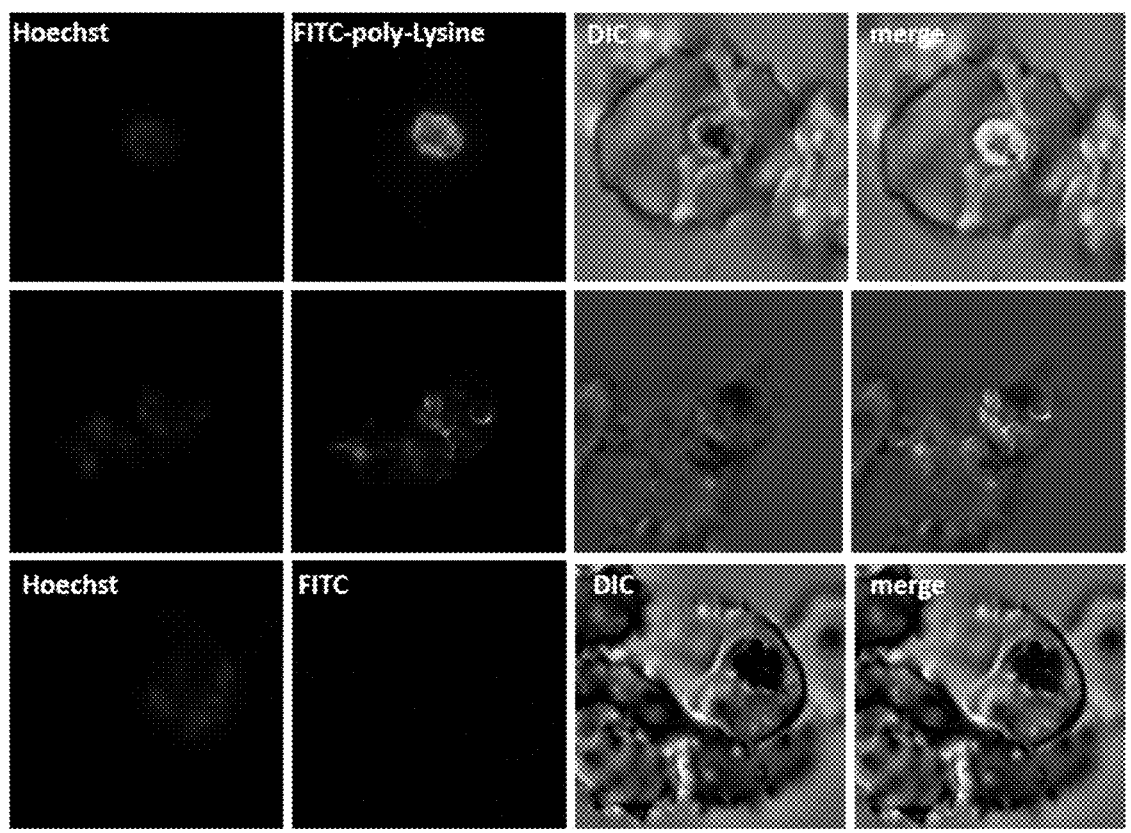

FIG. 19. Binding of FITC-labeled poly-lysine to infected erythrocytes, *P. falciparum* merozoites. Fast binding kinetics (order of 1-3 minutes).

Figure 20:
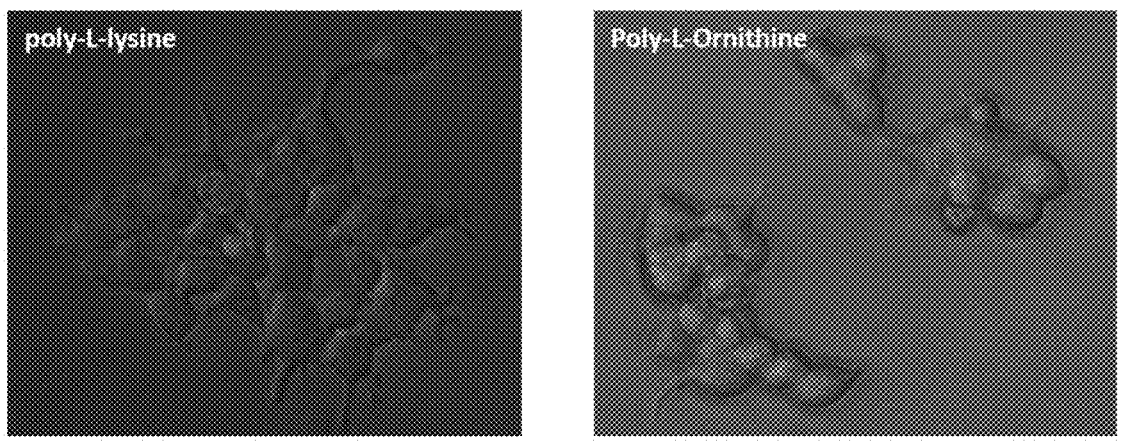

FIG. 20. Poly-L-lysine and poly-L-ornithine do not detectably bind to other human cells (uninfected human cells).

Figure 21:
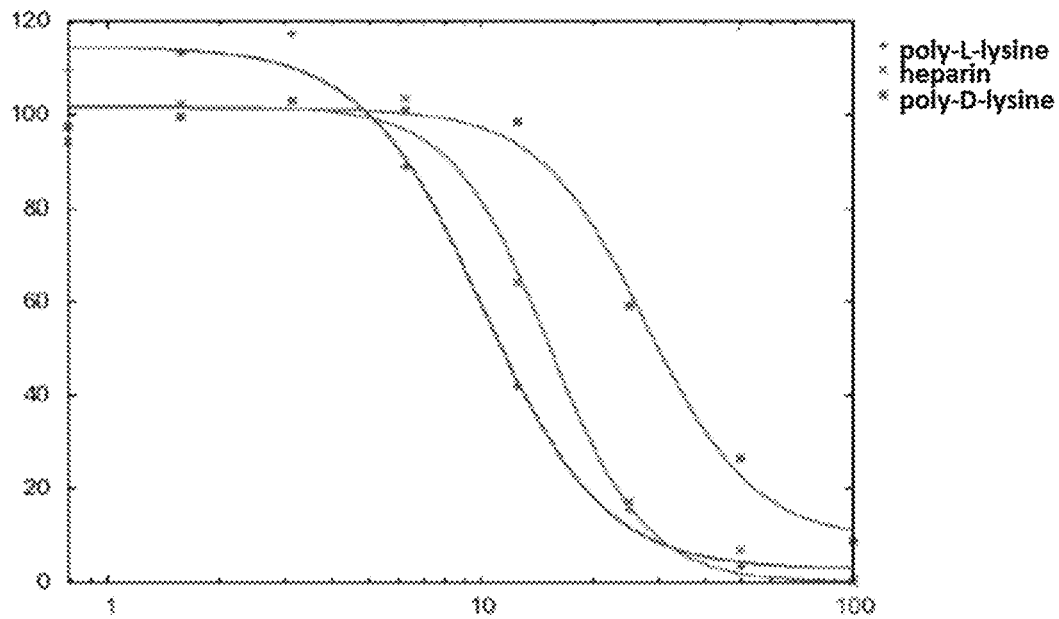

FIG. 21. $IC_{50}$ of polybasic peptides is better than heparin (reduced when compared to heparin).

Figure 22:
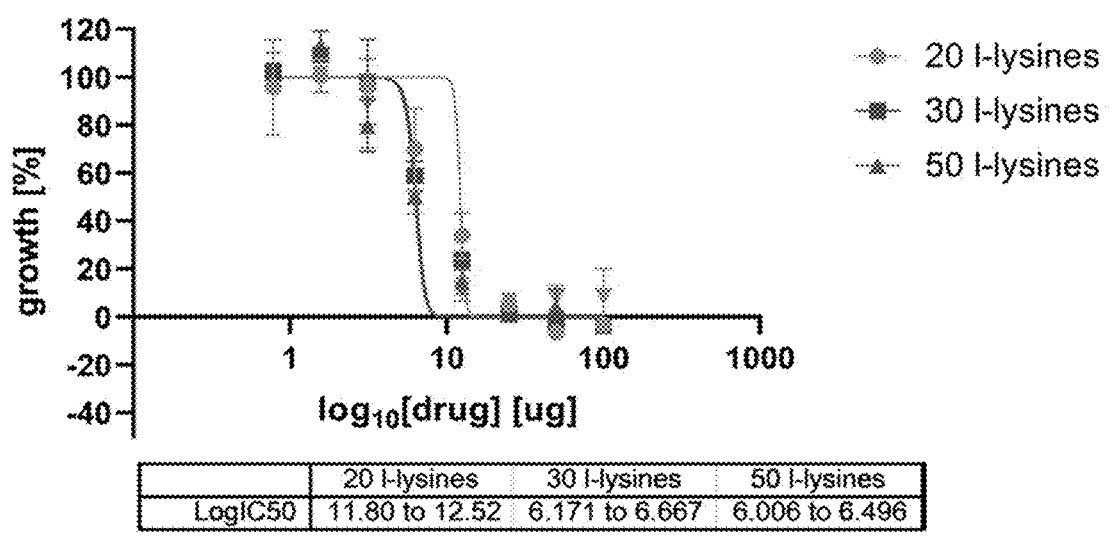

FIG. 22. Polybasic peptide of length 20 (SEQ ID NO: 3), 30 (SEQ ID NO: 2) or 50 (SEQ ID NO: 1) L-lysines. Shorter runs of polybasic peptides are less potent (10-L-lysines (SEQ ID NO: 4) and less have no activity).

Figure 23:
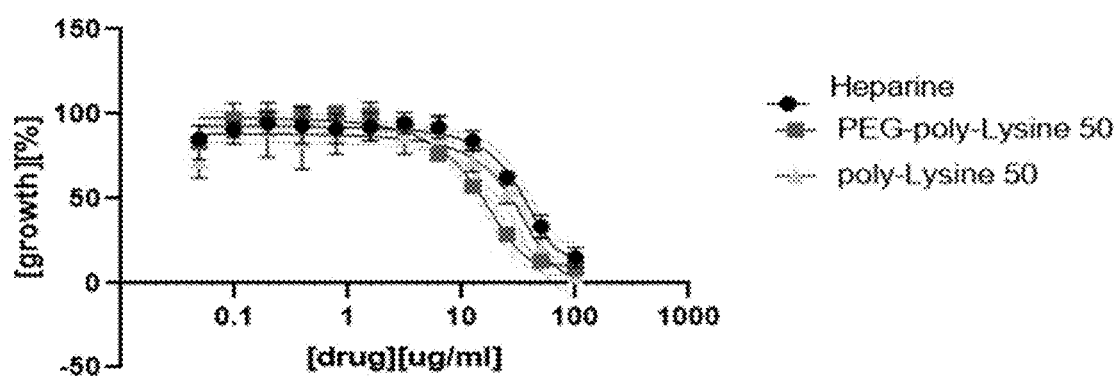
Figure 23:
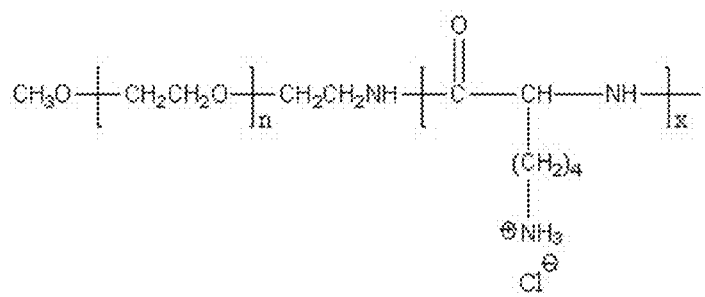

FIG. 23. PEGylation of Poly-Lys generally increases stability of peptides. Poly-L-lysine of length 50 (SEQ ID NO: 1) bloodstream half-life is 30 min. PEGylated-pLys up to 14 h in rats. It was surprising that poly-ε-L-lysine was not shown to be effective against malaria.

FIG. 24. Poly-L-lysine should target multiple targets and different types of Malaria parasites.

Figure 25:
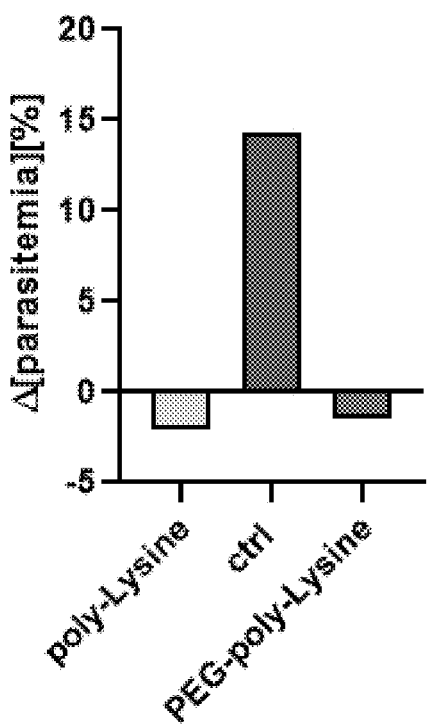
Figure 25:
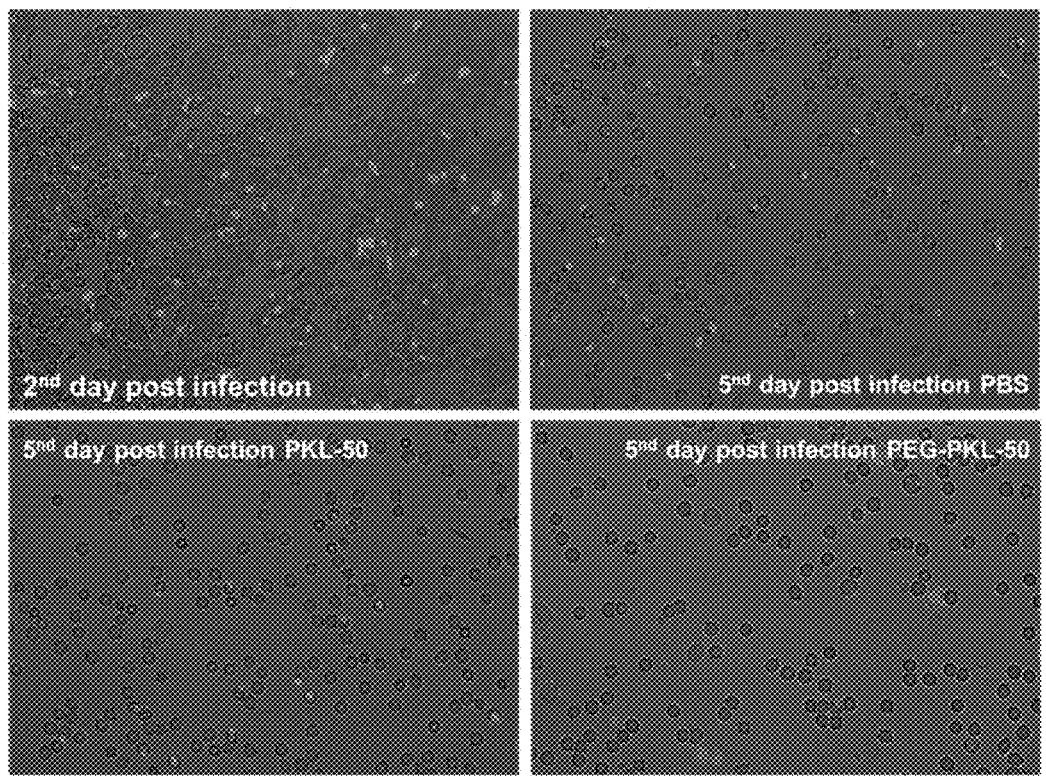

FIG. 25. Intraperitoneal treatment of mice results in the reduction of parasitemia over 2 days. Treatment of mice infected with mCherry labelled *P. berghei* with 4 doses of poly-lysine peptides or PEGylated poly-lysine polymers reduces parasitemia over 7 days of infection.

Figure 26:
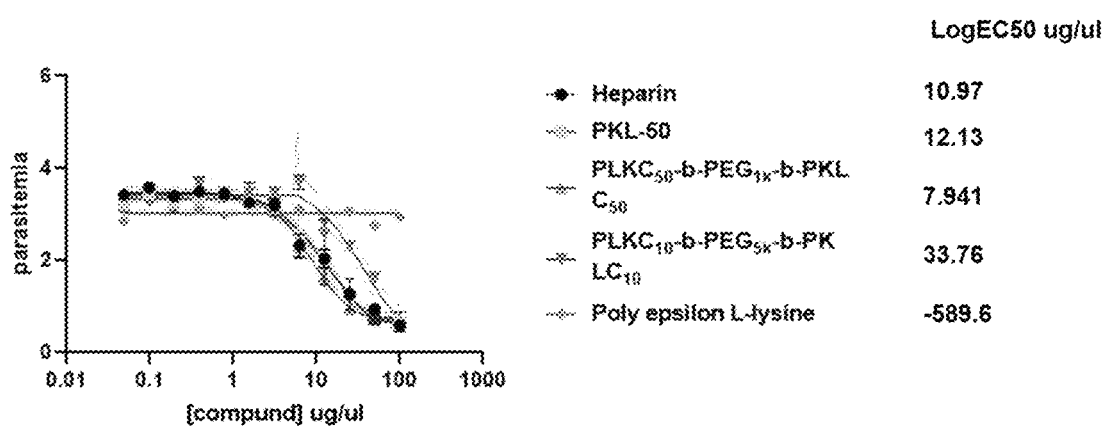
Figure 26:
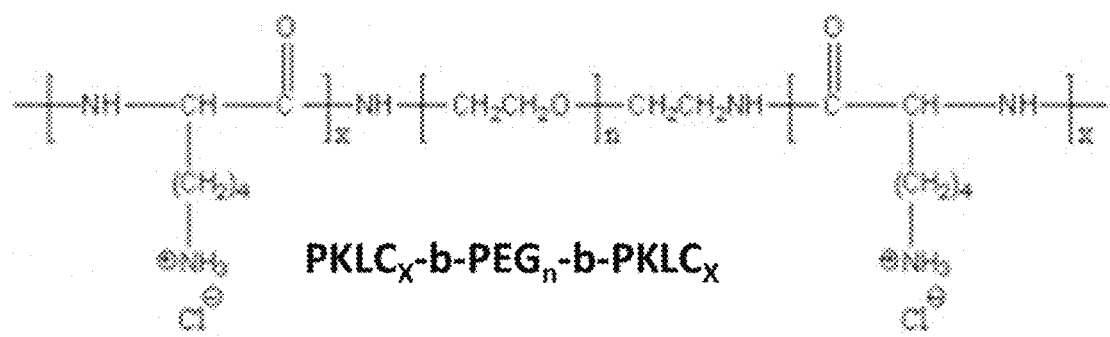

FIG. 26. Plot showing activity of PLK-PEG-PLK compositions. Epsilon poly-lysine did not appear to have activity against *Plasmodium*.

DETAILED DESCRIPTION OF THE INVENTION

The present disclosure is based, at least in part, on the discovery that polybasic peptides and polymers can be used as antimalarial drugs. As shown herein, polybasic peptides and polymers can be used for the treatment of *Plasmodium falciparum* and other *plasmodium* species that cause human malaria. Polybasic peptides and polymers reduce infection of human erythrocytes by parasites by blocking cellular adhesion of parasites to cells as well as directly interacting with parasite membranes. Additionally, polybasic peptides and polymers may block sequestration of infected erythrocytes in defined human organs (i.e., brain, liver among the others). $IC_{50}$ for poly-Lys and poly-ornithine is less than 10 μg/ml without hemolysis, compared with an $IC_{50}$ of 12 μg/ml for heparin. Poly-L-lysine $IC_{50}$ is 9 μg/ml. The $IC_{50}$ is the concentration of an inhibitor where the response (or binding) is reduced by half. It was shown herein (see e.g., FIG. 21) that the $IC_{50}$ of polybasic peptides are improved (reduced) compared to heparin.

Although previous studies have shown heparin can be used for malaria treatment, heparin is negatively charged, where the present polybasic antimalarial agents are positively charged (or have a net positive charge).

*Plasmodium falciparum*, the causative agent of human malaria, is an apicomplexan parasite with a complex, multi-host life cycle. Sixty percent of transcripts from its extreme AT-rich (81%) genome possess coding polyadenosine (polyA) runs, distinguishing the parasite from its hosts and other sequenced organisms. Recent studies indicate that transcripts with polyA runs, encoding for polylysine, are hot spots for ribosome stalling and frameshifting, eliciting mRNA surveillance pathways and attenuating protein synthesis in the majority of prokaryotic and eukaryotic organisms. Using bioinformatic and biochemical approaches, this work demonstrates that both endogenous genes and reporter sequences containing polyA tracks are efficiently and accurately transcribed and translated in *P. falciparum* cells. Translation of polyA tracks in the parasite does not elicit any response from mRNA surveillance pathways usually seen in host human cells or organisms with similar AT content (e.g., Tetrahymena *thermophila*), indicating a unique role of the parasite ribosomes in the evolution and adaptation of the *P. falciparum* protein synthesis machinery to not only an AU-rich transcriptome, but also the resulting polybasic amino sequences. Finally, this work shows that the ability of

*P. falciparum* to synthesize long poly-lysine repeats, usually encoded by polyA tracks, has given parasites an advantage in pathogenesis and infectivity through increased cellular adhesion.

This work has further measured the half maximal inhibitory concentration ($IC_{50}$) of different polybasic peptides and polymers with different lengths (e.g., 1,000 kDa-15,000 kDa) in in vitro assays with de-identified human erythrocytes and two strains of *Plasmodium falciparum* (Dd2 and Nf54). Polybasic peptides have an $IC_{50}$ of less than 10 μg/ml and prevent re-infection of human erythrocytes as well as control growth of *P. berghei* in mice model of malaria (see e.g., FIG. 25). PEGylated polybasic polymers can be used with higher efficiency as shown in FIG. 23, FIG. 25 and FIG. 26).

Polybasic peptides can be used as therapeutic or lead substances for new drugs for malaria. It is presently believed that there is no known current treatment of malaria with polybasic peptides and polymers.

It was being studied how and why *Plasmodium falciparum* (malaria parasite) can synthesize long poly lysine repeats from long polyA tracks. It was discovered that parasites use these repeats to adhere to erythrocytes and increase infection rate. This can be blocked by adding a polybasic protein, polybasic peptide, or polybasic polymer (e.g., poly-lysine, poly-ornithine or poly-arginine repeats, but not with poly-glutamate or other polymers that do not have positive charge). As such it is currently understood that a polybasic polymer of certain size could be used for treatment of malaria. Here is presented in vitro data with cultured human erythrocytes and malaria parasites to support this.

Polybasic Antimalarial Agent

As described herein, a polybasic antimalarial agent can comprise a polybasic compound, a polybasic protein, a polybasic peptide, a polybasic polymer, or a polybasic amino acid polymer.

For example, the polybasic antimalarial agent, such as a polybasic amino acid polymer, can comprise two or more basic amino acid monomers. As an example, a basic amino acid can be arginine (Arg), lysine (Lys), histidine (His), or ornithine (Orn). As another example, the polybasic antimalarial agent can comprise a polybasic amino acid polymer such as poly-L-lysine, poly-D-lysine, or poly-L-ornithine.

Generally, conservative substitutions can be made at any position so long as the required activity is retained. So-called conservative exchanges can be carried out in which the amino acid which is replaced has a similar property as the original amino acid, for example the exchange of Glu by Asp, Gln by Asn, Val by lie, Leu by lie, and Ser by Thr. For example, amino acids with similar properties can be Aliphatic amino acids (e.g., Glycine, Alanine, Valine, Leucine, Isoleucine); Hydroxyl or sulfur/selenium-containing amino acids (e.g., Serine, Cysteine, Selenocysteine, Threonine, Methionine); Cyclic amino acids (e.g., Proline); Aromatic amino acids (e.g., Phenylalanine, Tyrosine, Tryptophan); Basic amino acids (e.g., Histidine, Lysine, Arginine); or Acidic and their Amide (e.g., Aspartate, Glutamate, Asparagine, Glutamine). Deletion is the replacement of an amino acid by a direct bond. Positions for deletions include the termini of a polypeptide and linkages between individual protein domains. Insertions are introductions of amino acids into the polypeptide chain, a direct bond formally being replaced by one or more amino acids. Amino acid sequence can be modulated with the help of art-known computer simulation programs that can produce a polypeptide with, for example, improved activity or altered regulation. On the basis of this artificially generated polypeptide sequences, a corresponding nucleic acid molecule coding for such a modulated polypeptide can be synthesized in-vitro using the specific codon-usage of the desired host cell.

Conservative Substitutions I

| Side Chain Characteristic | Amino Acid |
|---|---|
| Aliphatic Non-polar | G A P I L V |
| Polar-uncharged | C S T M N Q |
| Polar-charged | D E K R |
| Aromatic | H F W Y |
| Other | N Q D E |

Conservative Substitutions II

| Side Chain Characteristic | Amino Acid |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Tur, Ser |
| Val (V) | Ile, Leu, Met, Phe, Ala |

The polybasic antimalarial agents, as described herein can be polymers comprising two or more monomers (e.g., repeating subunits). Polymers, both natural and synthetic, are created via polymerization of many small molecules, known as monomers. A polymer can be a homopolymer or a copolymer. A polymer can be a straight chain or a branched polymer. The length of the polymer can be quantified in terms of chain length (degree of polymerization or the number of monomers incorporated into the chain) or molecular weight (e.g., expressed in terms of weighted average, number-average molecular weight ($M_n$), or weight-average molecular weight ($M_w$)). As described herein, the polybasic antimalarial agent can have an average molecular weight between about 1 kDa and about 100 kDa or weight between about 1 kDa and about 15 kDa. Even though larger polymers could have potential toxicity issues for use in humans, larger and shorter polymers can be used for impregnation of anti-mosquito nets that are currently used to prevent malaria spreading.

As described herein, polybasic amino acids can be polymerized at the α or the ε position (e.g., α-poly-L-lysine (PLL), α-poly-D-lysine (PDL), ε-poly-D-lysine (EPD)).

As described herein, the polybasic antimalarial agent can be a polybasic peptide or polybasic polymer comprising greater than about 10 basic amino acids. For example, the polybasic antimalarial agent can be a polybasic peptide comprising between about 10 and about 150 basic amino acids (or an average between about 10 and about 150 basic amino acids), between about 15 and about 50 basic amino acids (or an average between about 15 and about 50 basic amino acids), or up to about 150 residues (about 150 kDa). As another example, the polybasic antimalarial agent can comprise basic amino acid repeats.

The polybasic antimalarial agent can comprise an amount of non-basic amino acids, while retaining anti-malarial activity.

As described herein, the polybasic antimalarial composition (e.g., polybasic polymers) can comprise or be conjugated to PEG (e.g., polyethylene glycol, monomethoxy PEG, polyethylene oxide (PEO), polyoxyethylene (POE)). The molecular weight (e.g., average molecular weight, weight average molecular weight (Mw), or its number average molecular weight ($M_n$)) of PEG can be between about 300 g/mol and about 40,000 g/mol. PEG can be in a branched, a star, or a comb configuration. The PEG can have between about n=0 and about n=150 units, preferably up to about 113 units (MW between about 0 kDa and 5 kDa).

Malaria

As described herein are compositions and methods of treating malaria. Malaria can be caused by a parasite. For example, the parasite can be a *Plasmodium* parasite. Species of *Plasmodium* parasites can be *Plasmodium falciparum* (or *P. falciparum*) (human host), *Plasmodium vivax* (or *P. vivax*) (human host), *Plasmodium knowlesi* (or *P. knowlesi*) (human host), or *Plasmodium yoelii* (or *P. yoelii*) (mouse host). Other species of *Plasmodium* parasites can be targeted by the polybasic compositions described herein can be *Plasmodium berghei, Plasmodium chabaudi*, or *Plasmodium cynomolgi*.

As an example, the parasite, *Plasmodium falciparum* causes malaria and utilizes polybasic peptides for infection, making it a therapeutic target. About 75% of *Plasmodium falciparum* genes have polyA tracks. The 75% of genes have sequences that have polyA tracks (runs of 12 adenosine nucleotides interrupted by one non-adenosine nucleotide G, C, or T). There are more than 140 proteins that have more than nine lysine residues in a row. Some of them have multiple "lysine tracks" (runs of 6 and more lysine residues in a row.

*Plasmodium falciparum* can express poly-lysine from polyA rich mRNA. *P. falciparum* has endogenous genes with the longest stretch of adenosine nucleotides is 132As coding for 44 lysine residues in a row.

Malaria infection can develop into anemia, hypoglycemia, or cerebral malaria. Cerebral malaria can cause coma and life-long-learning disabilities.

Current malaria drugs have limited target (hemozoin). The most common antimalarial drugs are derivatives of quinine such as Chloroquine (Aralen), Quinine sulfate (Qualaquin), Hydroxychloroquine (Plaquenil), Mefloquin, or combination of atovaquone and proguanil (Malarone). The majority of drugs have strong adverse effects such as hallucinations, hemolytic anemia, toxicity, or hypotension. Current therapies cannot be used in groups that are most affected such as pregnant women, young children, older people, or immune compromised individuals.

Mosquitos can also be treated with the polybasic antimalarial compositions as described herein. It has been shown that treating female mosquitoes with an antimalarial drug stopped parasites from developing inside the insects (Paton et al. 2019 Nature (567) 239-243). The polybasic antimalarial agents described herein can be used to treat or impregnate a net or netting (such as anti-mosquito netting, bed nets) walls, fabrics, or in sugar baits, for example. The polybasic antimalarial agents can be combined with other antimalarial agents or insecticides.

Formulation

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject. The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intratumoral, intranasal, inhalation (e.g., in an aerosol), implanted, intramuscular, intraperitoneal, intravenous, subcutaneous, intranasal, epidural, ophthalmic, transdermal, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described further below. Thus, in addition to the therapies described herein, one may also provide to the subject other therapies known to be efficacious for treatment of the disease, disorder, or condition.

| ICH Stability Zones | |
| --- | --- |
| Zone | Type of Climate |
| Zone I | Temperate zone |
| Zone II | Mediterranean/subtropical zone |
| Zone III | Hot dry zone |
| Zone IVa | Hot humid/tropical zone |
| Zone IVb | Hot/higher humidity |

| Long-Term Testing Conditions | | | |
| --- | --- | --- | --- |
| Climatic Zone | Temperature | Humidity | Minimum Duration |
| Zone I | 21° C. ± 2° C. | 45% RH ± 5% RH | 12 Months |
| Zone II | 25° C. ± 2° C. | 60% RH ± 5% RH | 12 Months |
| Zone III | 30° C. ± 2° C. | 35% RH ± 5% RH | 12 Months |
| Zone IVa | 30° C. ± 2° C. | 65% RH ± 5% RH | 12 Months |
| Zone IVb | 30° C. ± 2° C. | 75% RH ± 5% RH | 12 Months |
| Refrigerated | 5° C. ± 3° C. | No Humidity | 12 Months |
| Frozen | −15° C. ± 5° C. | No Humidity | 12 Months |

Crystalline PLL has a melting point of 142.2° C. and preserves structure at 37° C. Rhodamine dextran-lysine is also binding to parasites in infected erythrocytes. Oral drug delivery of linear PLL or dendrimers is in the range of 5-10% for blood over 6 hours period.

Therapeutic Methods

Also provided is a process of treating or preventing malaria in a subject in need administration of a therapeutically effective amount of a polybasic antimalarial agent (e.g., comprising a polybasic compound, polybasic protein, polybasic peptide, or polybasic polymer), so as to reduce infection.

Methods described herein are generally performed on a subject in need thereof. A subject in need of the therapeutic methods described herein can be a subject having, diagnosed with, suspected of having, or at risk for developing or contracting malaria. A determination of the need for treatment will typically be assessed by a history and physical exam consistent with the disease or condition at issue. Diagnosis of the various conditions treatable by the methods described herein is within the skill of the art. The subject can be an animal subject, including an insect, such as a mosquito, a mammal, such as horses, cows, dogs, cats, sheep, pigs, mice, rats, monkeys, hamsters, guinea pigs, and chickens, and humans. For example, the subject can be a human subject.

Generally, a safe and effective amount of a polybasic antimalarial agent is, for example, that amount that would cause the desired therapeutic effect in a subject while minimizing undesired side effects. In various embodiments, an effective amount of a polybasic antimalarial agent described herein can substantially inhibit a malaria infection, slow the progress of a malaria infection, or limit the development of a malaria infection. In various embodiments, an effective amount of a polybasic antimalarial agent described herein can substantially inhibit the ability of a *Plasmodium* parasite to proliferate, slow the progress of a *Plasmodium* parasite's ability to proliferate, or limit the ability of a *Plasmodium* parasite to proliferate by decreasing the ability for cellular adhesion.

For example, suppressing the *Plasmodium* parasite growth or infectivity can be inhibiting the ability of a *Plasmodium* parasite to proliferate or inhibiting the ability of a *Plasmodium* parasite to grow and can be achieved by decreasing the ability of the parasite to adhere to a cell (see e.g., Example 1).

In some embodiments, a therapeutically effective amount of a polybasic antimalarial agent can be between about 2 µg/kg body weight and about 50 mg/kg body weight. The effective dose ($IC_{50}$) can be between about 0.3 µM and about 1.5 µM.

According to the methods described herein, administration can be parenteral, pulmonary, oral, topical, intradermal, intramuscular, intraperitoneal, intravenous, subcutaneous, intranasal, epidural, ophthalmic, buccal, or rectal administration.

When used in the treatments described herein, a therapeutically effective amount of a polybasic antimalarial agent can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to substantially inhibit a malaria infection, slow the progress of a malaria infection, or limit the development of a malaria infection.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, $4^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Again, each of the states, diseases, disorders, and conditions, described herein, as well as others, can benefit from compositions and methods described herein. Generally, treating a state, disease, disorder, or condition includes delaying the appearance of clinical symptoms in a mammal afflicted with the state, disease, disorder, or condition but does not yet experience or display clinical or subclinical symptoms thereof. Treating can also include inhibiting the state, disease, disorder, or condition, e.g., arresting or reducing the development of the disease or at least one clinical or subclinical symptom thereof. Furthermore, treating can include relieving the disease, e.g., causing regression of the state, disease, disorder, or condition or at least one of its clinical or subclinical symptoms. A benefit to a subject to be treated can be either statistically significant or at least perceptible to the subject or to a physician.

Administration of a polybasic antimalarial agent can occur as a single event or over a time course of treatment. For example, a polybasic antimalarial agent can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for malaria.

A polybasic antimalarial agent can be administered simultaneously or sequentially with another agent, such as an antibiotic, an anti-inflammatory, or another agent. For example, a polybasic antimalarial agent can be administered simultaneously with another agent, such as an antibiotic or an anti-inflammatory. Simultaneous administration can occur through administration of separate compositions, each containing one or more of a polybasic antimalarial agent, an antibiotic, an anti-inflammatory, or another agent. Simultaneous administration can occur through administration of one composition containing two or more of a polybasic antimalarial agent, an antibiotic, an anti-inflammatory, or another agent. A polybasic antimalarial agent can be administered sequentially with an antibiotic, an anti-inflammatory, or another agent. For example, a polybasic antimalarial agent can be administered before or after administration of an antibiotic, an anti-inflammatory, or another agent.

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

As discussed above, administration can be parenteral, pulmonary, oral, topical, intradermal, intramuscular, intraperitoneal, intravenous, subcutaneous, intranasal, epidural, ophthalmic, buccal, or rectal administration.

Agents and compositions described herein can be administered in a variety of methods well known in the arts. Administration can include, for example, methods involving oral ingestion, direct injection (e.g., systemic or stereotactic), implantation of cells engineered to secrete the factor of interest, drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 m), nanospheres (e.g., less than 1 m), microspheres (e.g., 1-100 m), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition can be administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; or improve shelf life of the product.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present disclosure.

Having described the present disclosure in detail, it will be apparent that modifications, variations, and equivalent embodiments are possible without departing the scope of the present disclosure defined in the appended claims. Furthermore, it should be appreciated that all examples in the present disclosure are provided as non-limiting examples.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: *Plasmodium Falciparum* Translational Machinery Condones Polyadenosine Repeats This example describes the adaptation of *Plasmodium falciparum* to an adenosine (A)- and uracil (U)-rich (AU-rich) transcriptome and how poly-lysine repeats enable enhanced cellular adhesion of parasites and interaction of parasite with erythrocytes. This discovery of an infectious pathway enabled the innovative use of polybasic compositions as antimalarial agents. As described herein, polybasic compositions (e.g., compounds, proteins, peptides, and polymers) can block this interaction, thereby reducing infection.

*Plasmodium falciparum*, the causative agent of human malaria, is an apicomplexan parasite with a complex, multi-host life cycle. Sixty percent of transcripts from its extreme AT-rich (81%) genome possess coding polyadenosine (polyA) runs, distinguishing the parasite from its hosts and other sequenced organisms. Recent studies indicate that transcripts with polyA runs encoding poly-lysine are hot spots for ribosome stalling and frameshifting, eliciting mRNA surveillance pathways and attenuating protein synthesis in the majority of prokaryotic and eukaryotic organisms. Using bioinformatic and biochemical approaches, this work demonstrates that both endogenous genes and reporter sequences containing long polyA runs are efficiently and accurately transcribed and translated in *P. falciparum* cells. Translation of polyA tracks in the parasite does not elicit any response from mRNA surveillance pathways usually seen in host human cells or organisms with similar AT content. The translation efficiency and accuracy of the parasite protein synthesis machinery reveals a unique role of ribosomes in the evolution and adaptation of *P. falciparum* to an AU-rich transcriptome and polybasic amino sequences. Finally, this work shows that the ability of *P. falciparum* to synthesize long poly-lysine repeats has given this parasite a unique protein exportome and an advantage in infectivity that can be suppressed by addition of exogenous poly-basic polymers.

Background

The complex life cycle of *Plasmodium falciparum*, responsible for 90% of all malaria-associated deaths, involves multiple stages in both human and mosquito hosts. Asexual replication during the intraerythrocytic development cycle (IDC) is tightly regulated over a 48-hour period and involves the expression of the majority of its genes. Progression through asexual stages (ring, trophozoite, schizont) of the IDC requires a strictly controlled panel of gene expression profiles for each stage. A range of 16-32 daughter cells results from the IDC. Thus, a single, originating merozoite must undergo several rounds of DNA synthesis, mitosis, and following nuclear division in a relatively short period. The apparent necessity for rapid and accurate DNA replication, RNA transcription, and protein translation, as well as competent folding machinery, is further emphasized by the demonstration that genes important for these processes are essential in *P. falciparum*. Even so, faithful execution of these fundamental processes is challenged by the AT-rich *P. falciparum* genome: averaging ~81% overall AT content: ~90% in the non-coding region and, a still relatively high, ~76% within the coding region. Recently, it was demonstrated that the translation of genes with polyadenosine runs (polyA tracks), primarily coding for lysine residues, is attenuated in the majority of tested eukaryotic and prokaryotic organisms due to ribosomal stalling and frameshifting on such RNA motifs. In humans, the presence of just 12 adenosines in an mRNA coding region will deplete the protein synthesis of a given gene by more than 40%. The consequence of translational arrest is activation of one or more mRNA surveillance mechanisms, which has been demonstrated in studies of human, yeast and *E. coli*.

High AT-content within coding regions and an extreme AAA and AAT codon bias increases the propensity for polyA tracks in the *P. falciparum* transcriptome. Additionally, a "just-in-time" transcriptional model of gene expression in *P. falciparum* has been proposed whereby a transcriptional burst produces most of the gene transcripts required for the IDC during the trophozoite stage. While both the DNA and RNA polymerases must contend with high DNA AT-content, the unusual AU-richness of *Plasmodium* mRNAs also impacts the fidelity and efficacy of protein synthesis. With "just-in-time" translation of numerous A-rich coding sequences and poly-lysine proteins harboring an AAA codon bias, expressed at all stages in the parasite life cycle, the *Plasmodium* translation machinery represents a paradigm-breaking system in protein synthesis compared to other organisms. Given the high impact of possible changes on both nucleic acid and protein metabolism, driven by enrichment of polyA and poly-lysine sequences, *Plasmodium* species have likely adapted their protein synthesis machinery to this trait. Furthermore, such evolutionary inherited features in the *P. falciparum* parasite have likely resulted in survival and reproduction benefits for this organism in its particular environment(s).

In this study, the translational efficiency and accuracy of protein synthesis from polyA tracks in *P. falciparum* cells was determined and how the translational machinery may have evolved to accommodate the unusual AU-richness of the *P. falciparum* transcriptome was explored. Furthermore, the benefits of poly-lysine repeats, resulting from the translation of polyA tracks, on parasite RNA metabolism, survival, and pathogenicity was determined.

Results

Figure 1B:
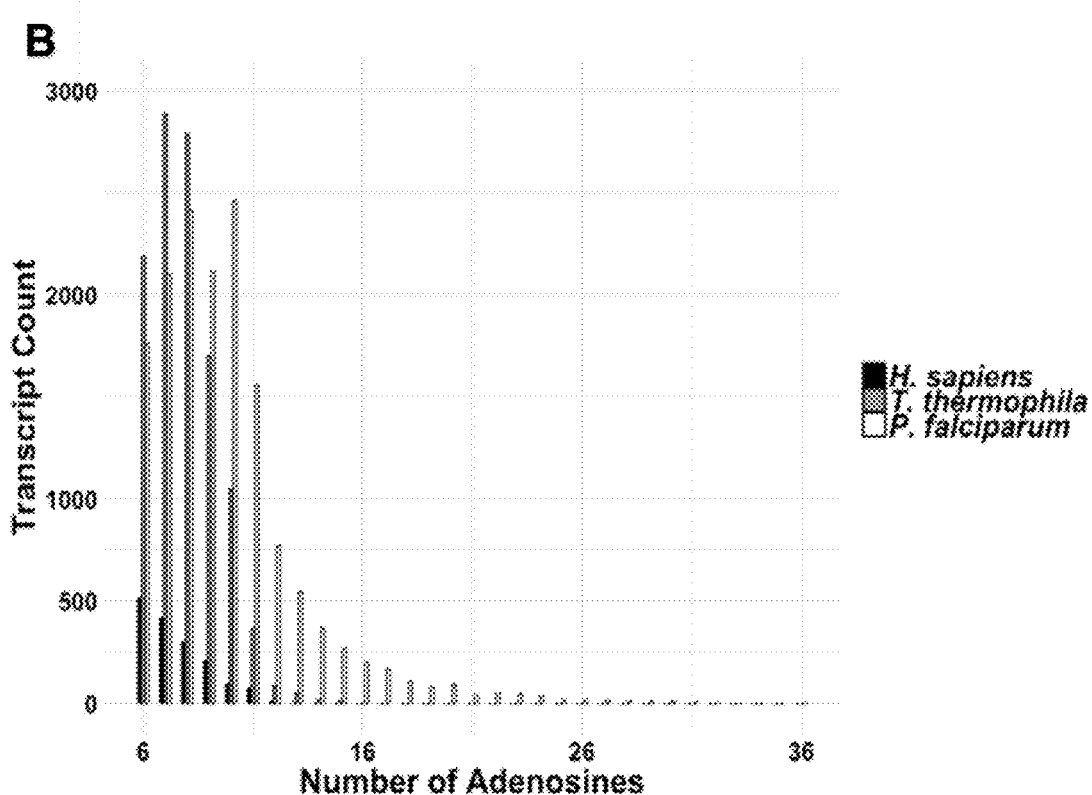

While the reasons for the disproportionate representation of the four nucleotides in any given genome may be different, the shift towards extreme AT- or GC-richness must be accommodated by adaptation of the transcription and translation apparatuses; this enables the cell to transcribe and translate each gene appropriately. Characterization of gene organization in *P. falciparum* revealed that both coding and non-coding regions contribute equally to overall AT-richness of its genome. To explore the association between polyA tracks—focusing on ≥12 adenosine nucleotides in coding sequences that have previously been shown to induce stalling, as well as genomic AT-content—250 eukaryotic genomes were analyzed (see e.g., FIG. 1A). As hypothesized, *P. falciparum* and genus affiliates have a much higher ratio of polyA track genes when normalized to genomic AT-content. This feature of *Plasmodium* species is conserved regardless of their genomic AT-content, resulting in two groups (low and high AT-content *Plasmodium* spp.) with unusually high portions of polyA track genes ranging from 35% to over 60% of the total transcriptome. To further emphasize the differences between *P. falciparum* and other organisms, genes that contain polyA tracks and their full length were also analyzed (see e.g., FIG. 5 and FIG. 1B, respectively).

Figure 1C:
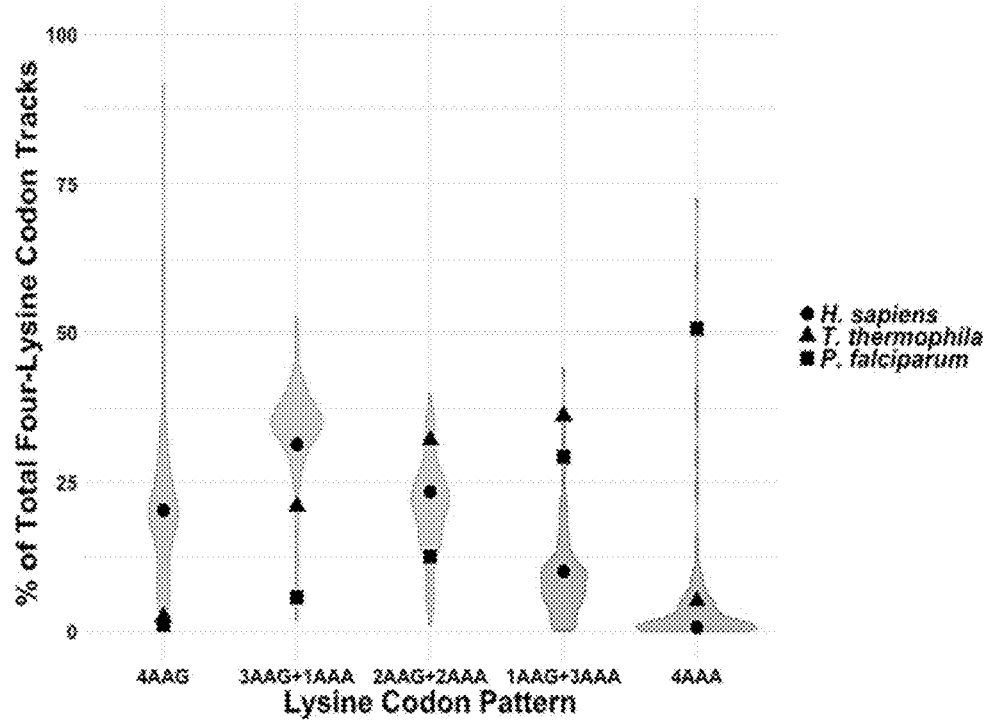
Figure 5:
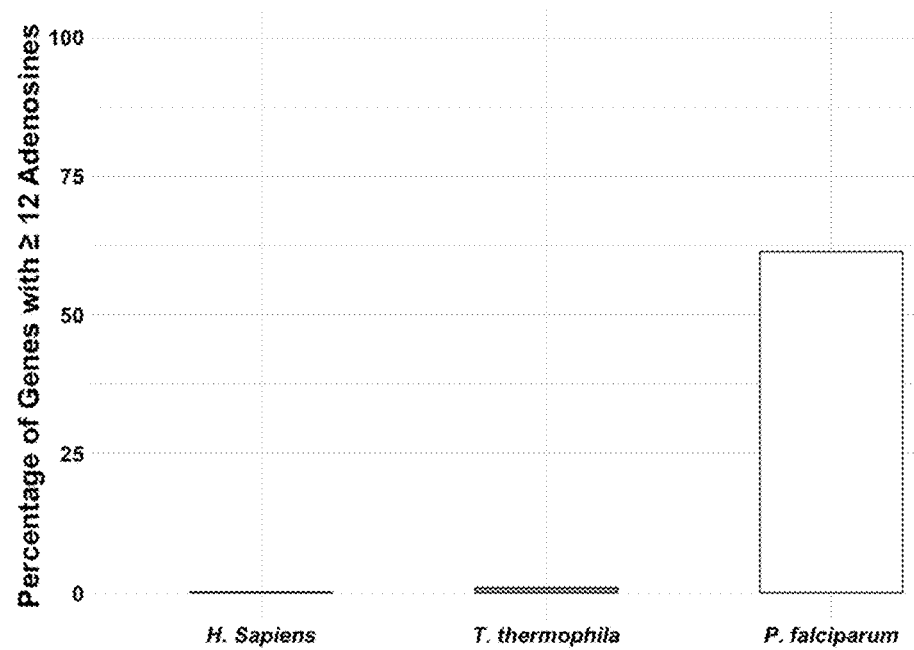
Figure 6:
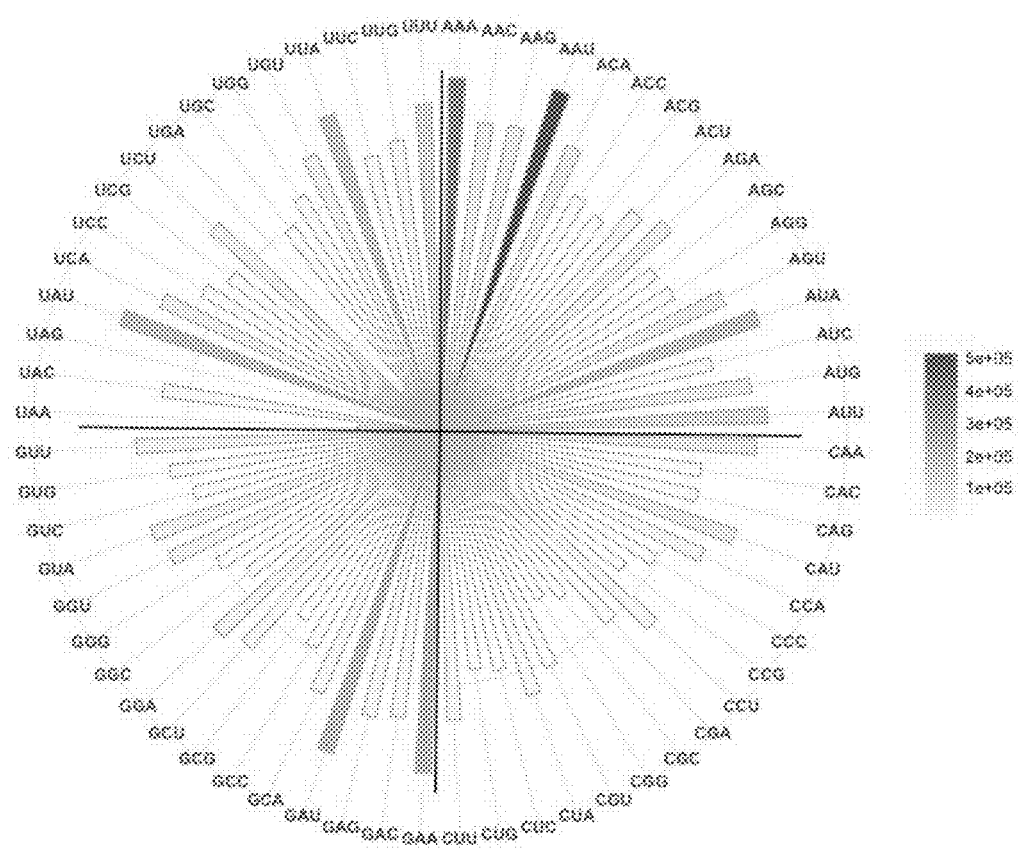

In comparison to the human host and Tetrahymena thermophila, another protozoan with an AT-rich genome, P. falciparum showed an immense amount of polyA track genes (12 adenosine nucleotides allowing for one mismatch—12A-1, FIG. 5). Around 60% of genes in P. falciparum have ≥12 A's in a row, while humans and T. thermophila range from just 2-5%. This difference is even more apparent in transcript counts that host polyA tracks (see e.g., FIG. 1B). The P. falciparum genome contains more than 1000 genes with 16 consecutive adenosine nucleotides (16As); reaching a maximum of 111 As in P. falciparum fch 4 strain (see e.g., FIG. 1C).

The observed disparity in the number of genes with polyA tracks could be due to previously observed codon bias in P. falciparum. However, has been shown previously that codon bias and tRNA abundance do not correlate with codon selection in genes coding for lysine repeats. To investigate in more detail the distribution of AAA and AAG codons in polylysine tracts, transcripts from P. falciparum and other eukaryotic genomes were analyzed (see e.g., FIG. 1C). A complete reversal of the trend exhibited in other organisms was observed, including humans and T. thermophila, with the highest abundance of P. falciparum transcripts hosting four consecutive AAA codons in stretches of four lysine residues (see e.g., FIG. 1C). This divergence from other analyzed transcriptomes is preserved in other members of Plasmodium spp., with P. berghei being an extreme example using only AAA codons in 73% of transcripts coding for poly-lysine stretches. A majority of Plasmodium poly-lysine proteins fall into the group of essential genes based on the recent mutagenesis studies. This outcome is expected given that gene ontology results indicate enrichment in gene products involved in the crucial cellular process such as translation initiation, chromosome segregation, previously observed in other organisms as well as in cellular and pathological cell adhesion. Interestingly, cellular and pathological adhesion genes that are the hallmark of Plasmodium infectivity and pathogenicity came as the only enriched biological process in gene ontology search with polyA track carrying genes (see e.g., TABLE 1).

Previous analysis indicated that 70%-85% of orthologs of polyA carrying genes from P. falciparum have the same polyA segments in genes from other Plasmodium species, regardless of their genomic AT content. This high level of conservation is not found in other organisms arguing for the possible functional role of polyA tracks and poly-lysine repeats within Plasmodium species. As such, bioinformatic analyses demonstrated that conservation of both polyA tracks in the transcriptome and poly-lysine repeats in the proteome of P. falciparum have been evolutionary selected and conserved due to the possible benefits for the parasite.

Figure 2A:
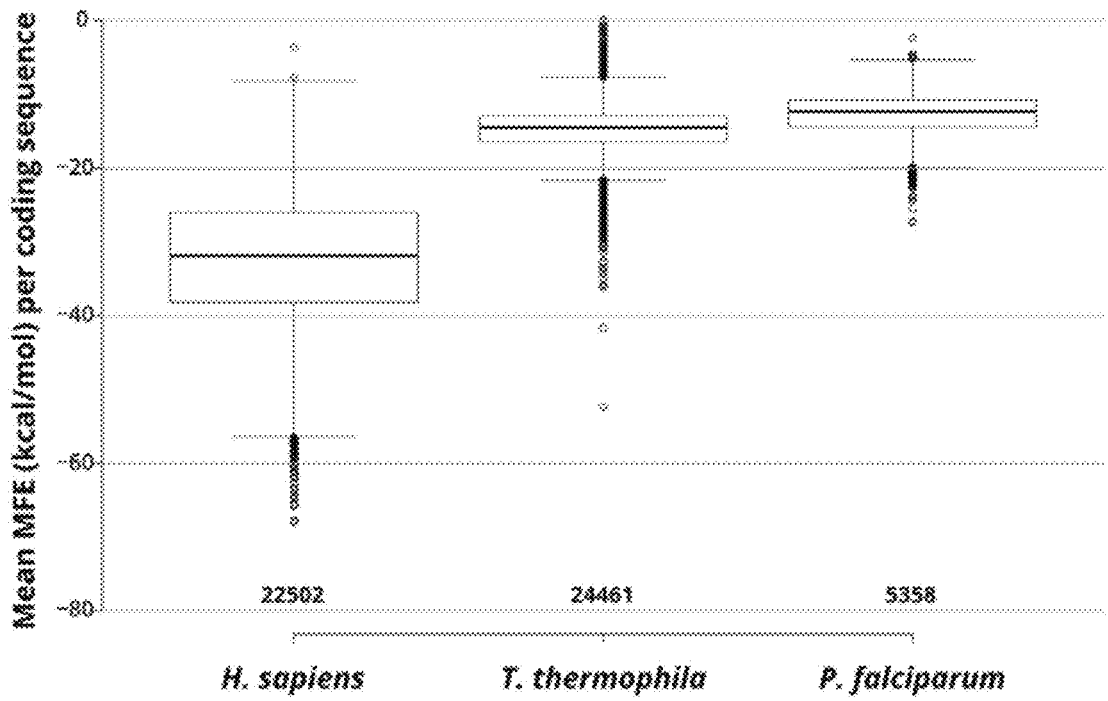
Figures 2B, 2C:
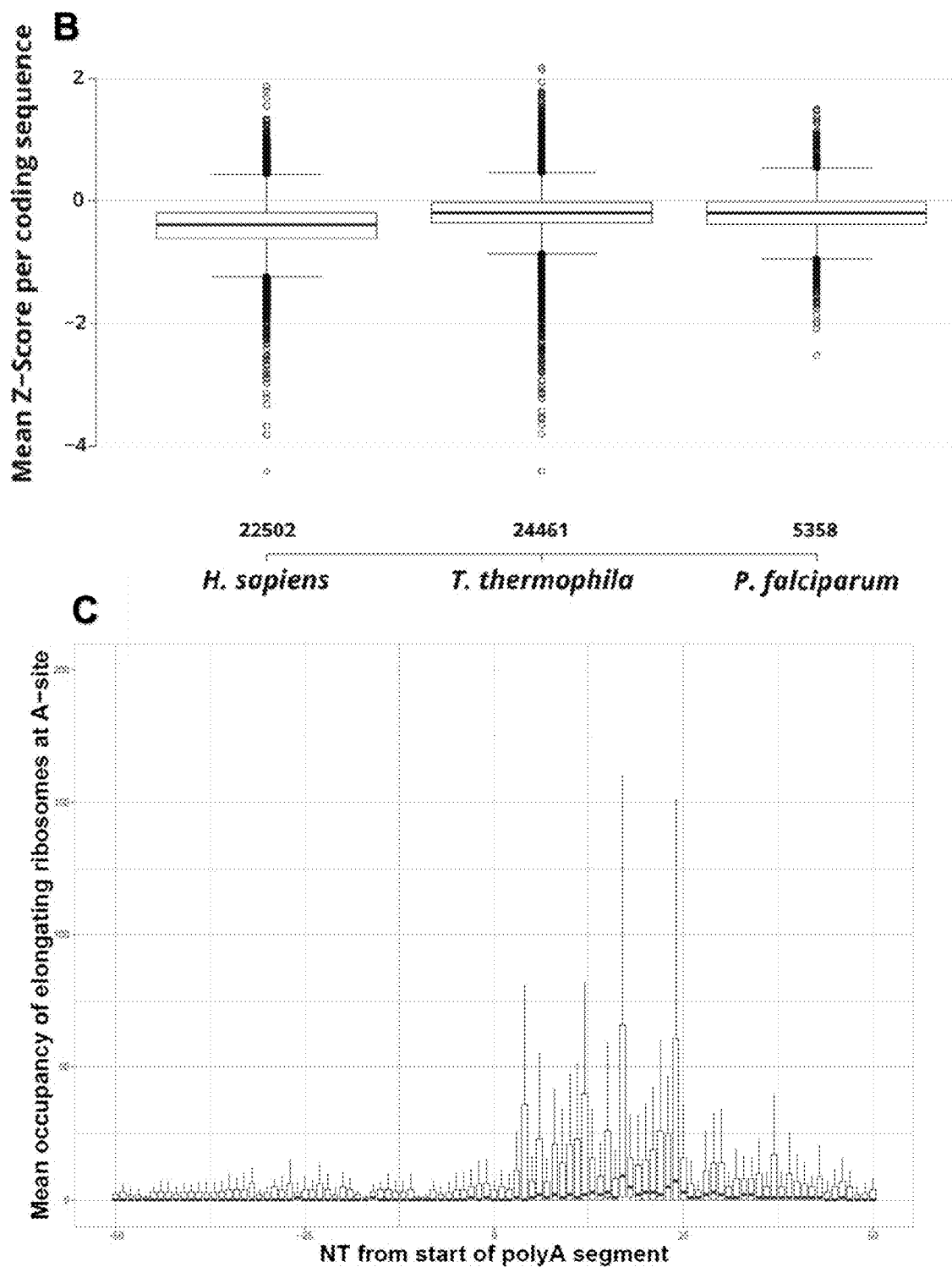

Given the diversity of RNA functions, mRNA stability and successful translation are made possible, and affected, by the ability of RNA to fold into unique functional structures. Shifts towards AU-/GC-richness may affect the propensity and stability of RNA structures thermodynamically. This possible effect on RNA begs the question as to whether or not the presence of polyA tracks, and thereby poly-lysine repeats, provide important effects on mRNA structure and, subsequently, protein synthesis in P. falciparum. To examine how high AU-content influences predicted mRNA structure and stability in different organisms, the ability of all mRNAs to form thermodynamically stable structures was compared and their stability was calculated using in silico approaches. The coding transcripts from T. thermophila and P. falciparum had on average higher (less stable) predicted minimum free energy (see e.g., FIG. 2A) of folding than transcripts from human; possibly due to the AU-bias of these organisms. Interestingly transcriptome z-scores—measuring the difference in stability of native vs. random sequence—from the same organisms revealed no significant differences between mRNAs from each (see e.g. FIG. 2B). This result indicates that while folding stability varies greatly between species (following from the skews in nucleotide content), the propensity of native sequences to be ordered to fold, does not.

Figure 2D:
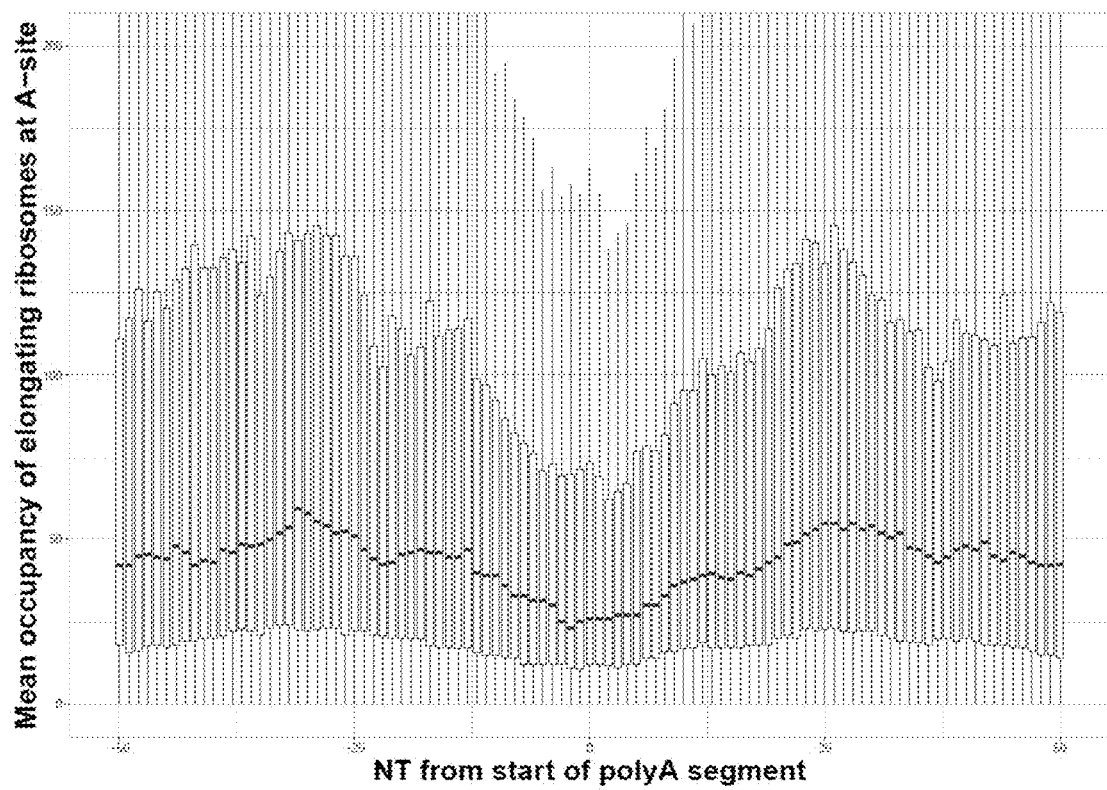
Figure 7:
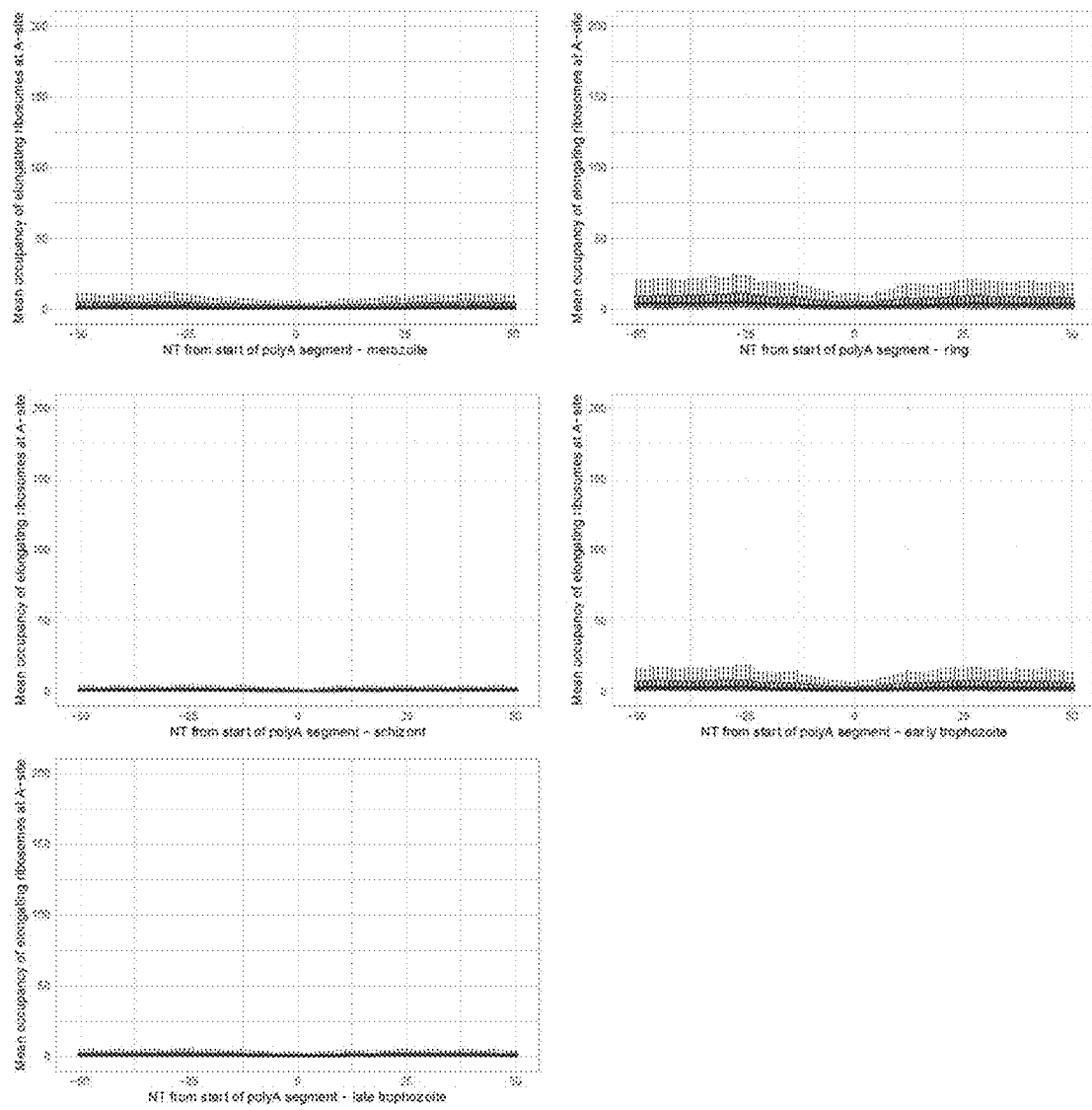

With as much as 60% of the parasite transcriptome harboring hot-spots of translational stalling, a comparative analysis of ribosome profiling data from P. falciparum was performed and data was aggregated for human tissues harmonized at GWIPS database to determine whether endogenous polyA tracks and poly-lysine sequences, induce translational pausing. Ribosome stalling can be observed in the ribosome profiling data as an increase in the abundance of ribosome footprints on sequences that cause ribosomes to pause during translation. Cumulative data for all transcripts with polyA tracks from human cells indicates substantial translational pausing on these sequences (see e.g., FIG. 2C). However, no evidence for ribosome stalling could be observed for P. falciparum transcripts accommodating polyA tracks with a length of ≤22 consecutive adenosine nucleotides (see e.g., FIG. 2D). This translation phenomenon is independent of different stages of P. falciparum intraerythrocytic development (see e.g., FIG. 7) and ostensibly irrespective of polyA track, or poly-lysine, length to such a degree that cumulative transcript analysis becomes hindered by low sequence complexity of this region or

TABLE 1

Highly significant gene ontology terms (GO) from biological process category for polyA-track carrying genes in Plasmodium falciparum.

Figure 8:
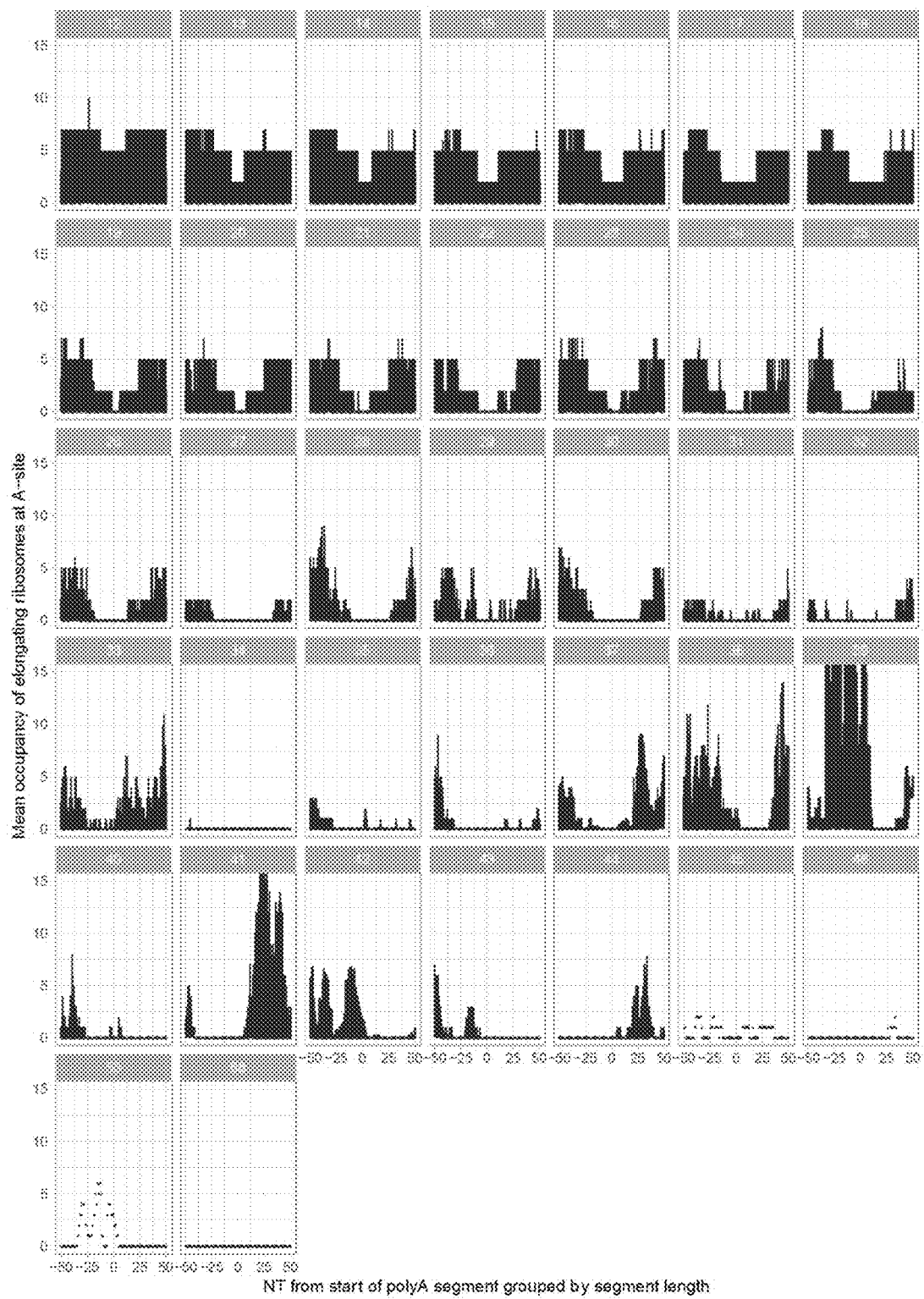
Figure 9:
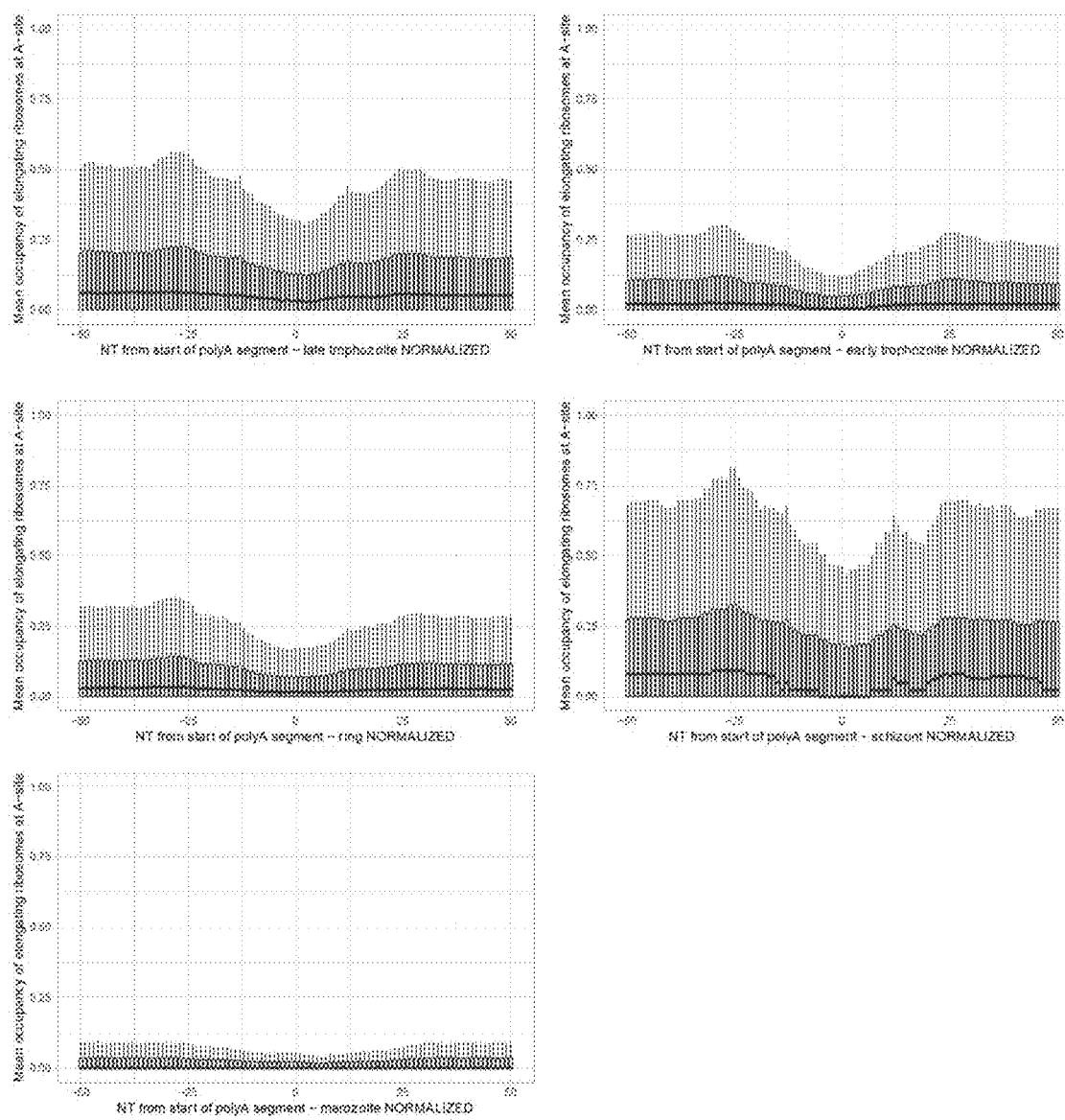

| ID | Name | Bgd count | Result count | Pct of bgd | Fold enrichment | Odds ratio | P-value | Benjamini | Bonferroni |
|---|---|---|---|---|---|---|---|---|---|
| GO:0016337 | single organismal cell-cell adhesion | 57 | 56 | 98.2 | 1.56 | 33.76 | 8.98E−11 | 6.69E−08 | 1.34E−07 |
| GO:0098602 | organism cell single adhesion | 57 | 56 | 98.2 | 1.56 | 33.76 | 8.98E−11 | 6.69E−08 | 1.34E−07 |
| GO:0007155 | cell adhesion | 77 | 71 | 92.2 | 1.47 | 7.15 | 2.66E−09 | 1.32E−06 | 3.97E−06 |
| GO:0009405 | pathogenesis | 101 | 81 | 80.2 | 1.28 | 2.44 | 0.00010834 | 0.04035608 | 0.16142433 | reduced number of reads for the long polyA tracks (see e.g., FIG. 8). While a relatively small increase in the number of elongating ribosomes is observed on polyA segments in the late trophozoite and schizont stages of IDC (see e.g., FIG. 9), it's unclear if these translate into larger protein expression.

Figure 10:
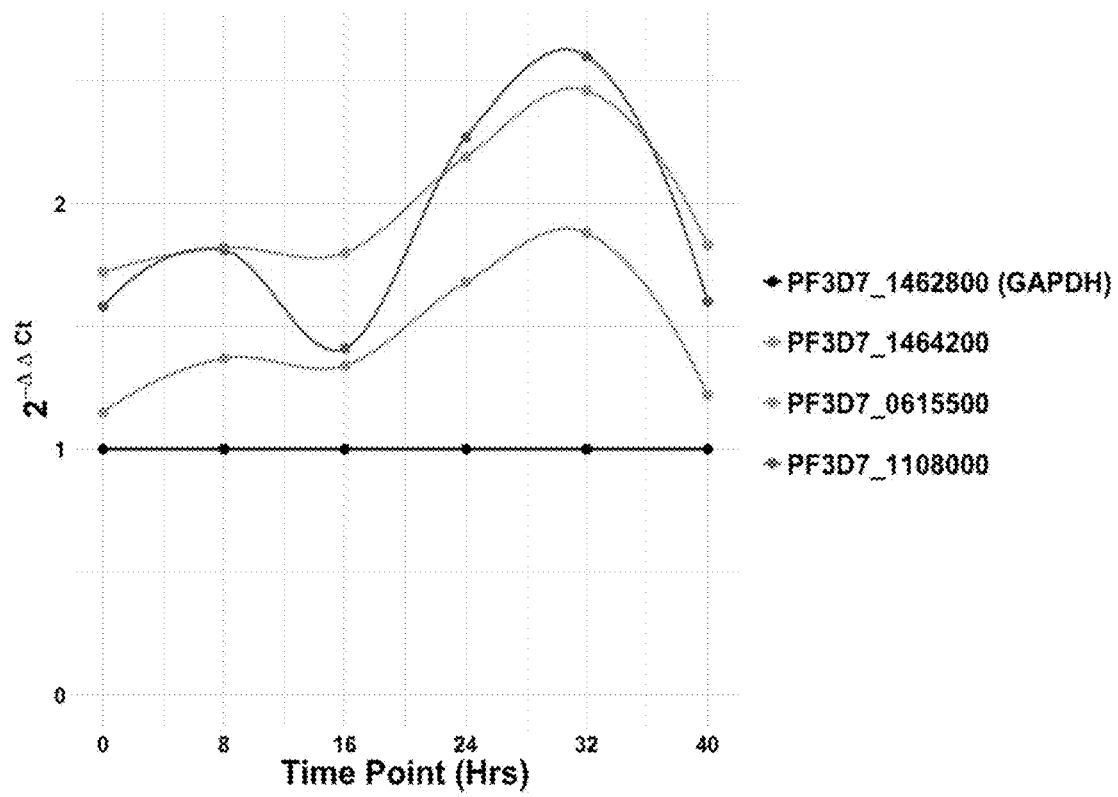

Given the potential for negative selection against polyA tracks, particularly in laboratory conditions, a small subset of varied length, differentially expressed polyA track-containing genes was selected for expression analysis (GAPDH—PF3D7_1462800 (control), 610-PF3D7_1464200 (longest polyA track length 20 As), CRK5-PF3D7_0615500 (longest polyA track length 20As of three present tracks), IWS1 L-PF3D7_1108000 (longest polyA track length 31As of two present tracks). Using qRT-PCR analysis of total RNA, the expression profiles of select endogenous genes in a *P. falciparum* Dd2 lab strain were analyzed. A time course study of synchronized parasite culture indicated that the selected polyA track transcripts are efficiently transcribed at all time points when compared to the control gene (see e.g., FIG. 10). Additionally, Sanger sequencing and gel analysis of cloned cDNAs on the selected subset of endogenous *P. falciparum* genes revealed that the annotated polyA tracks remained intact in the lab strain.

Figure 3A:
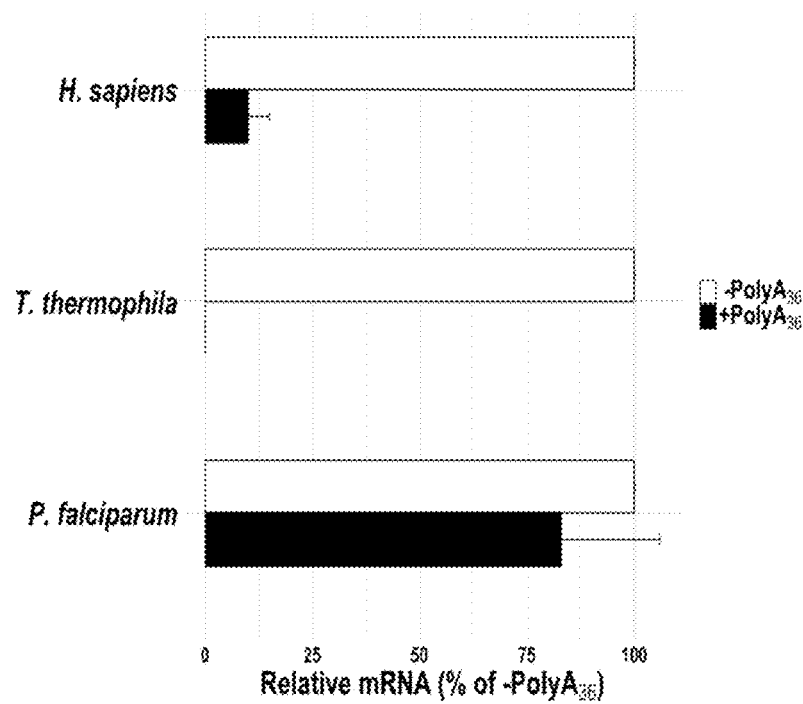
Figure 3B:
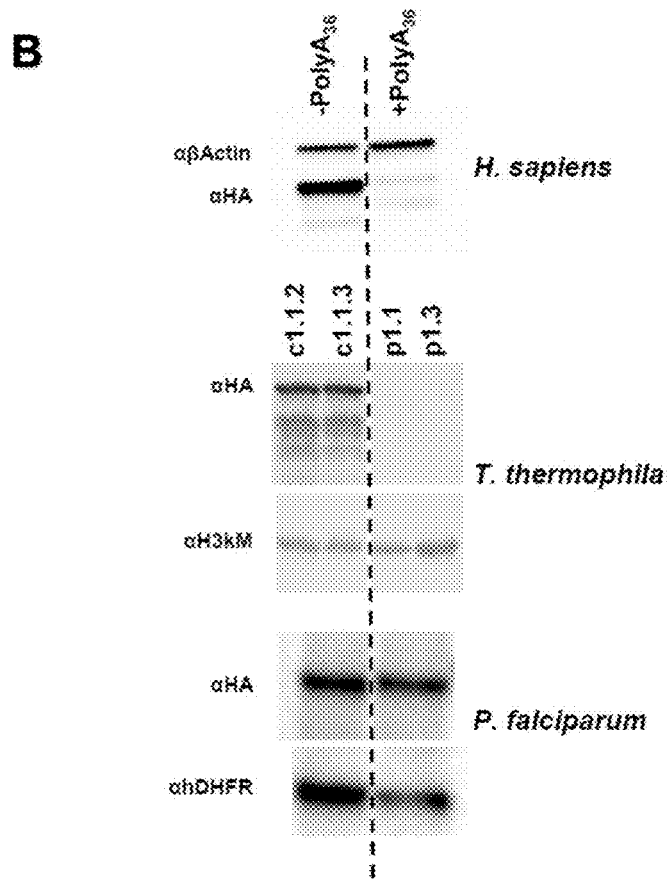
Figure 3C:
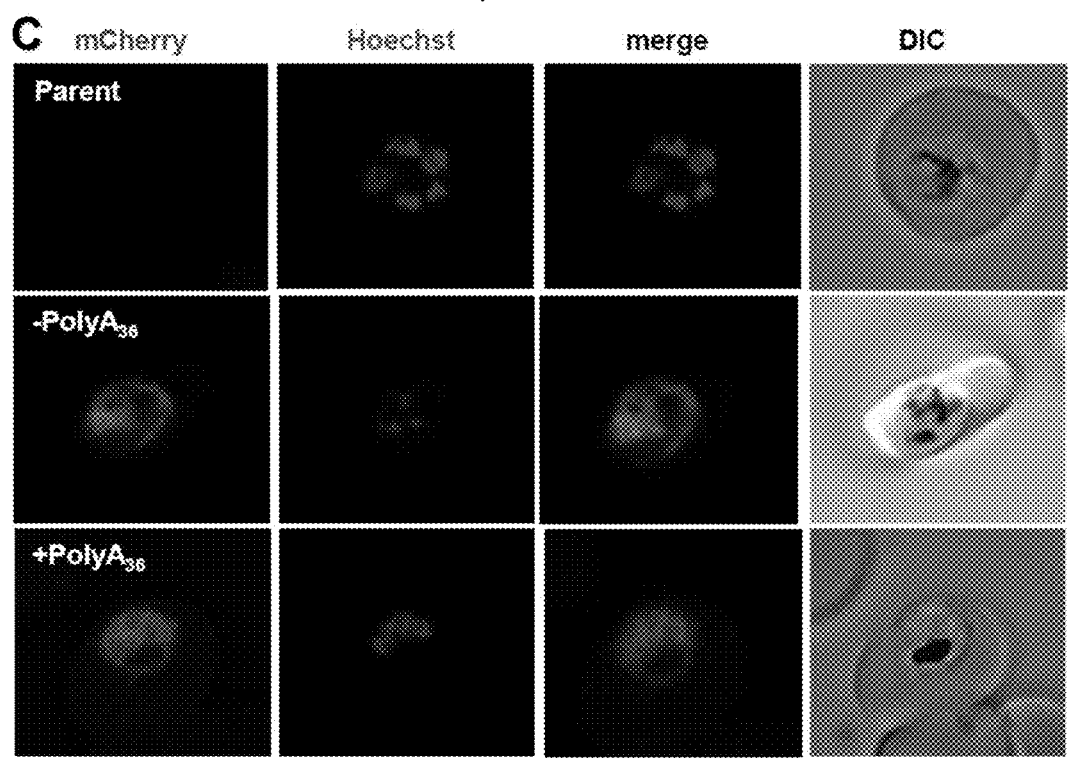
Figure 3D:
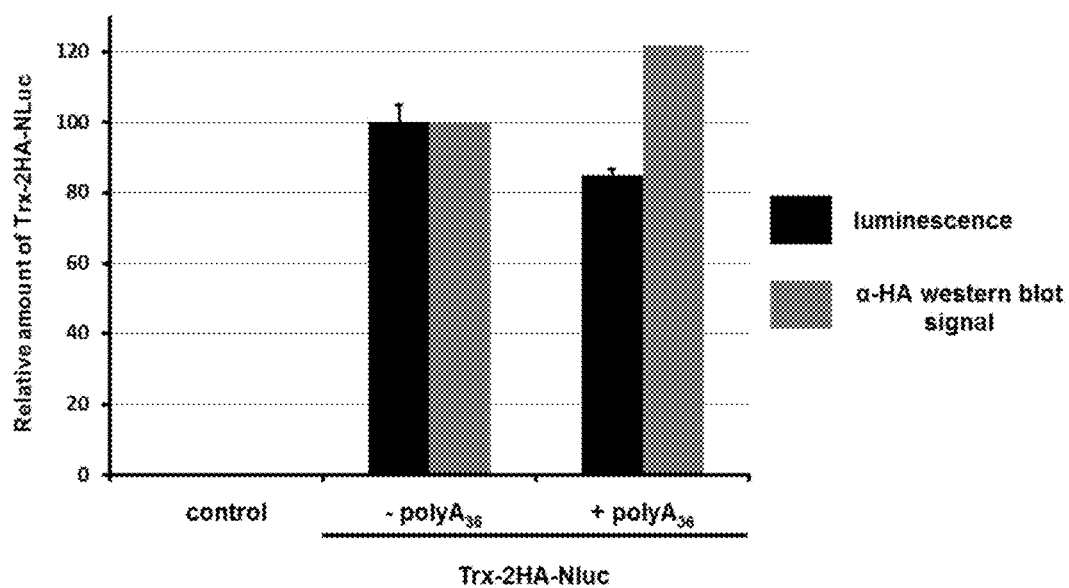

To investigate further the *P. falciparum* transcriptome feature that distinguishes it most from other organisms, double HA-tagged reporter constructs with a 36 adenosine nucleotide (36As) insertion, coding for 12 lysine residues, between the tag and a fluorescent protein were used (see e.g., FIG. 11). As a control, only HA-tagged reporter proteins were used. Episomal expression of the reporter in all three organisms was followed by analysis of RNA abundance by qRT-PCR and protein abundance by western blot detection of the HA-tag (see e.g., FIG. 3A and FIG. 3B, respectively). As expected, robust changes in mRNA levels (see e.g., FIG. 3A) and substantial losses in protein expression (see e.g., FIG. 3B) for reporters with polyA tracks in both neonatal human dermal fibroblasts (HDFs) and AT-genome rich *T. thermophila* were observed. Minimal, if any effects, of polyA track insertion on reporter mRNA and protein expression in *P. falciparum* were observed (see e.g., FIG. 3A and FIG. 3B). Further analysis of *P. falciparum* cells by live-fluorescence microscopy confirms equivalent mCherry reporter expression, judging by the intensity of fluorescence, between constructs with and without polyA tracks (see e.g., FIG. 3C). To assess whether the efficiency of polyA track translation is altered when located further downstream of the start codon, a construct was designed with thioredoxin and nano-luciferase (nanoluc) proteins separated with HA-tag and AAA-coded poly-lysine stretch (see e.g., FIG. 12A and FIG. 12B). Measurement of nanoluc luminescence from the same number of drug-selected parasites indicates slightly higher expression of a reporter with polyA track compared with control reporter (see e.g., FIG. 3D). The same ratio was observed in western blot analysis of protein, respectively (see e.g., FIG. 3D and FIG. 12A and FIG. 12B). Taken together, the ribosome profiling analyses, selected endogenous gene expression analysis, and reporter expression data (see e.g., FIG. 2A-FIG. 2D and FIG. 3A-FIG. 3D) indicate that polyA tracks are tolerated by the parasite translational machinery, and suggest an adaptation of the *P. falciparum* translation and mRNA surveillance machinery to its AU-rich transcriptome and poly-lysine rich proteome.

Figure 4A:
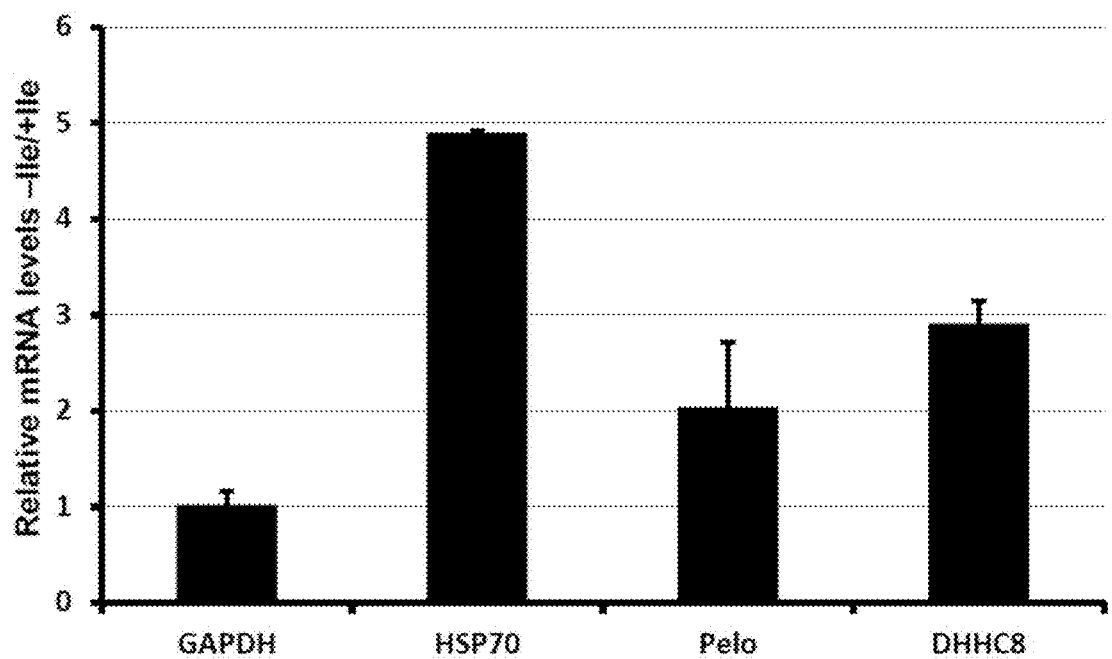
Figure 4B:
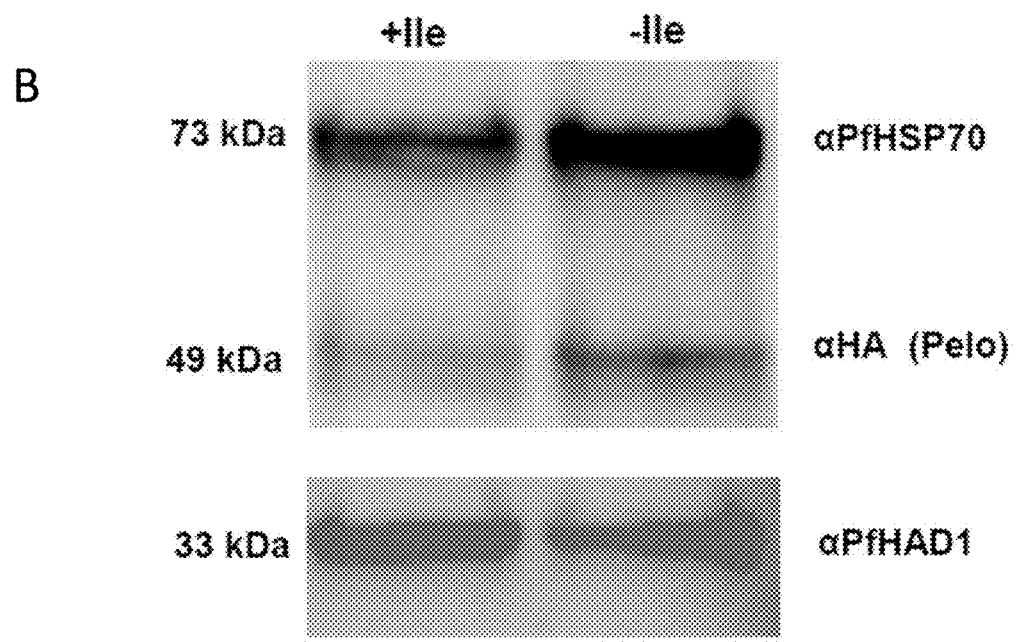

It has been shown the translation of polyA tracks elicits non-sense mediated decay (NMD) and "no-go" decay (NGD) mRNA surveillance pathways in other organisms. To test how *P. falciparum* has evolved and adapted to accommodate both polyA tracks and poly-lysine repeats, mRNA surveillance pathways and ribosomes were selected as principal components that control mRNA quality, as well as the fidelity and efficiency of protein synthesis. While previous work demonstrated that the NMD pathway is intact, the existence of the NGD pathway was previously untested in *P. falciparum*. To explore whether changes in the NGD pathway are potential adaptations of *P. falciparum* to polyA tracks and poly-lysine repeats, CRISPR/Cas9 technology was used to HA-tag the endogenous Pelota homolog (PfPelo, PF3D7_0722100) in *P. falciparum* Dd2 cells. The Pelo protein in complex with Hbs1, for which there is no clear homolog observed in *P. falciparum*, recognizes and rescues stalled ribosomes on long polyA stretches. Increased Pelota recruitment to polysome fractions is one of the indicators of a stalled protein synthesis while the transcripts responsible for ribosomal stalling are targeted for the mRNA decay. In the absence of sequences that directly stall *P. falciparum* ribosomes, isoleucine (Ile) starvation was used to assess the recruitment of PfPelo protein to stalled ribosomes. Ile starvation in *P. falciparum* was previously reported to induce a state of hibernation through the arrest of protein synthesis from which parasites could be recovered. It was found that expression of PfPelo and Hsp70 was upregulated in starved cells (see e.g., FIG. 4A and FIG. 4B) with a different localization pattern of the PfPelo protein in polysome profiles from the starved and controlled parasites. Interestingly, while PfPelo was recruited to polysome fractions in samples obtained from Ile starved *P. falciparum* cells, targeted degradation was not observed, but somewhat stabilization of Ile-rich transcripts: such as palmitoyltransferase DHHC8 (PF3D7_1321400), as compared to non-starved control samples. These results indicate that NGD components are being actively recruited to the stalled ribosomes; however, this process is independent of endonucleolytic cleavage of stalled mRNAs observed in the other organisms.

Figure 4C:
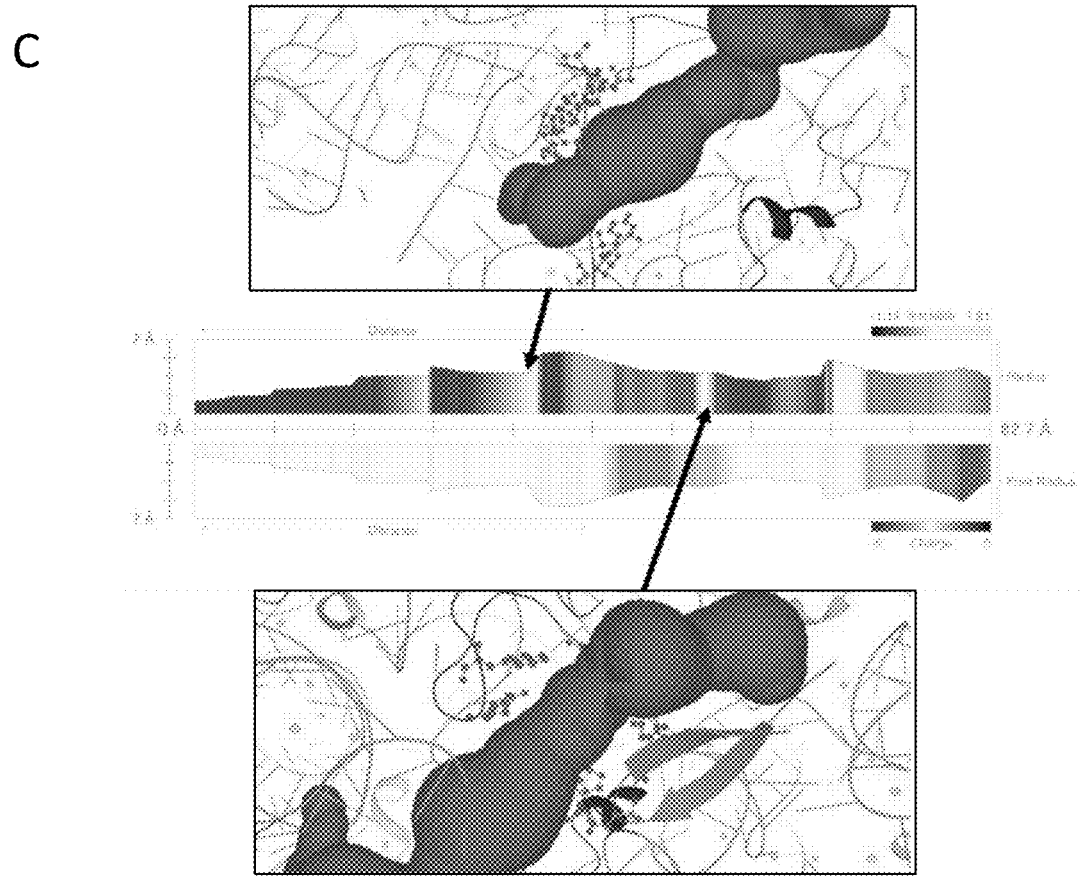

Recently, *P. falciparum* ribosomes were also shown to have different structural and dynamic features that distinguish them from other organisms; with the probable absence of RACK1 being one of the most prominent features regarding the translation of polyA tracks and poly-lysine repeats (see e.g., FIG. 13). Recent reports from yeast cells indicate the requirement of RACK1 proteins for endonucleolytic cleavage of stalled mRNAs. Additionally, deletion of RACK1 in human and yeast cells was also shown to increase production of proteins with polybasic peptides, however at the cost of increased frameshifting. To further investigate whether additional differences in the ribosome structure contributed to *P. falciparum* adaptation to long polyA tracks and poly-lysine repeats, ribosome exit channels were compared between human, yeast, extremophile archaea and *Plasmodium* (see e.g., FIG. 4C, FIG. 14, FIG. 15, and FIG. 16). Interestingly, two conserved patches of hydrophobic residues lining the exit channel (one being flanked by rRNA, while the other by ribosomal proteins L4 and L22) present in all four structures are almost barely noticeable in case of *Plasmodium* (see e.g., FIG. 4C). Given how unfavorable interactions are between clusters of positive charges and hydrophobic environments, this feature represents an interesting optimization of *P. falciparum* ribosomes that enables them to translate long poly-lysine repeats.

Conserved evolutionary adaptations result in traits that are beneficial for organisms. The increased AT-richness of *P. falciparum*, as such, could be a result of selective pressure on biosynthetic pathways (AT vs. GC biosynthesis) and the oxidative intraerythrocytic environment. Both of these environmental or cellular features would drive the genome towards higher AT content and, ultimately, increased polyA track length. However, whether benefits of *Plasmodium*'s increase in poly-lysine repeats might have different etiology was unknown. Gene ontology analyses were performed on polyA track and poly-lysine genes in *P. falciparum* and suggested that cellular and pathological adhesion proteins are one of the enriched gene groups between all exported proteins from *P. falciparum* (see e.g., TABLE 1 and TABLE 2).

TABLE 2

Highly significant gene ontology terms (GO) from biological process category for exported genes in *Plasmodium falciparum* (197 genes in total).

| ID | Name | Bgd count | Result count | Pct of bgd | Fold enrichment | Odds ratio | P-value | Benjamini | Bonferroni |
|---|---|---|---|---|---|---|---|---|---|
| GO:0044419 | interspecies interaction between organisms | 335 | 72 | 21.5 | 5.36 | 10.05 | 1.86E−36 | 8.28E−35 | 1.66E−34 |
| GO:0044403 | symbiosis, encompassing mutualism through parasitism | 335 | 72 | 21.5 | 5.36 | 10.05 | 1.86E−36 | 8.28E−35 | 1.66E−34 |
| GO:0051704 | multi-organism process | 381 | 75 | 19.7 | 4.91 | 9.15 | 2.44E−35 | 7.23E−34 | 2.17E−33 |
| GO:0020013 | modulation by symbiont of host erythrocyte aggregation | 190 | 51 | 26.8 | 6.69 | 11.71 | 4.20E−30 | 4.68E−29 | 3.74E−28 |
| GO:0034118 | regulation of erythrocyte aggregation | 190 | 51 | 26.8 | 6.69 | 11.71 | 4.20E−30 | 4.68E−29 | 3.74E−28 |
| GO:0034110 | regulation of homotypic cell-cell adhesion | 190 | 51 | 26.8 | 6.69 | 11.71 | 4.20E−30 | 4.68E−29 | 3.74E−28 |
| GO:0030155 | regulation of cell adhesion | 190 | 51 | 26.8 | 6.69 | 11.71 | 4.20E−30 | 4.68E−29 | 3.74E−28 |
| GO:0022407 | regulation of cell-cell adhesion | 190 | 51 | 26.8 | 6.69 | 11.71 | 4.20E−30 | 4.68E−29 | 3.74E−28 |
| GO:0044068 | modulation by symbiont of host cellular process | 192 | 51 | 26.6 | 6.62 | 11.54 | 7.35E−30 | 7.27E−29 | 6.54E−28 |
| GO:0044003 | modification by symbiont of host morphology or physiology | 193 | 51 | 26.4 | 6.58 | 11.46 | 9.70E−30 | 7.84E−29 | 8.63E−28 |
| GO:0051817 | modification of morphology or physiology of other organism involved in symbiotic interaction | 193 | 51 | 26.4 | 6.58 | 11.46 | 9.70E−30 | 7.84E−29 | 8.63E−28 |
| GO:0035821 | modification of morphology or physiology of other organism | 194 | 51 | 26.3 | 6.55 | 11.38 | 1.28E−29 | 9.47E−29 | 1.14E−27 |
| GO:00200033 | antigenic variation | 204 | 49 | 24 | 5.99 | 9.91 | 1.93E−26 | 1.22E−25 | 1.71E−24 |
| GO:0051809 | passive evasion of immune response of other organism involved in symbiotic interaction | 204 | 49 | 24 | 5.99 | 9.91 | 1.93E−26 | 1.22E−25 | 1.71E−24 |
| GO:0043207 | response to external biotic stimulus | 206 | 49 | 23.8 | 5.93 | 9.78 | 3.12E−26 | 1.26E−25 | 2.78E−24 |

TABLE 2-continued

Highly significant gene ontology terms (GO) from biological process category for exported genes in *Plasmodium falciparum* (197 genes in total).

| ID | Name | Bgd count | Result count | Pct of bgd | Fold enrichment | Odds ratio | P-value | Benjamini | Bonferroni |
|---|---|---|---|---|---|---|---|---|---|
| GO:0051832 | avoidance of defense of other organism involved in symbiotic interaction | 206 | 49 | 23.8 | 5.93 | 9.78 | 3.12E−26 | 1.26E−25 | 2.78E−24 |
| GO:0051707 | response to other organism | 206 | 49 | 23.8 | 5.93 | 9.78 | 3.12E−26 | 1.26E−25 | 2.78E−24 |
| GO:0051834 | evasion or tolerance of defense of other organism involved in symbiotic interaction | 206 | 49 | 23.8 | 5.93 | 9.78 | 3.12E−26 | 1.26E−25 | 2.78E−24 |
| GO:0051807 | evasion or tolerance of defense response of other organism involved in symbiotic interaction | 206 | 49 | 23.8 | 5.93 | 9.78 | 3.12E−26 | 1.26E−25 | 2.78E−24 |
| GO:0052173 | response to defenses of other organism involved in symbiotic interaction | 206 | 49 | 23.8 | 5.93 | 9.78 | 3.12E−26 | 1.26E−25 | 2.78E−24 |
| GO:0052564 | response to immune response of other organism involved in symbiotic interaction | 206 | 49 | 23.8 | 5.93 | 9.78 | 3.12E−26 | 1.26E−25 | 2.78E−24 |
| GO:0051805 | evasion or tolerance of immune response of other organism involved in symbiotic interaction | 206 | 49 | 23.8 | 5.93 | 9.78 | 3.12E−26 | 1.26E−25 | 2.78E−24 |
| GO:0009607 | response to biotic stimulus | 207 | 49 | 23.7 | 5.9 | 9.71 | 3.97E−26 | 1.54E−25 | 3.53E−24 |
| GO:0009605 | response to external stimulus | 214 | 49 | 22.9 | 5.71 | 9.29 | 2.04E−25 | 7.55E−25 | 1.81E−23 |
| GO:0065008 | regulation of biological quality | 263 | 51 | 19.4 | 4.83 | 7.55 | 6.61E−23 | 2.35E−22 | 5.88E−21 |
| GO:0051701 | interaction with host | 285 | 51 | 17.9 | 4.46 | 6.8 | 3.10E−21 | 1.06E−20 | 2.76E−19 |
| GO:0016337 | single organismal cell-cell adhesion | 57 | 23 | 40.4 | 10.06 | 18.32 | 3.18E−18 | 1.01E−17 | 2.83E−16 |
| GO:0098602 | single organism cell adhesion | 57 | 23 | 40.4 | 10.06 | 18.32 | 3.18E−18 | 1.01E−17 | 2.83E−16 |
| GO:0007155 | cell adhesion | 77 | 23 | 29.9 | 7.44 | 11.48 | 7.28E−15 | 2.23E−14 | 6.48E−13 |
| GO:0009405 | pathogenesis | 101 | 25 | 24.8 | 6.17 | 8.93 | 5.70E−14 | 1.69E−13 | 5.07E−12 |
| GO:0044406 | adhesion of symbiont to host | 165 | 30 | 18.2 | 4.53 | 6.15 | 9.42E−13 | 2.62E−12 | 8.39E−11 |

TABLE 2-continued

Highly significant gene ontology terms (GO) from biological process category for exported genes in *Plasmodium falciparum* (197 genes in total).

| ID | Name | Bgd count | Result count | Pct of bgd | Fold enrichment | Odds ratio | P-value | Benjamini | Bonferroni |
|---|---|---|---|---|---|---|---|---|---|
| GO:0020035 | cytoadherence to micro-vasculature, mediated by symbiont protein | 165 | 30 | 18.2 | 4.53 | 6.15 | 9.42E−13 | 2.62E−12 | 8.39E−11 |
| GO:0022610 | biological adhesion | 192 | 31 | 16.1 | 4.02 | 5.33 | 1.01E−11 | 2.72E−11 | 8.98E−10 |
| GO:0050896 | response to stimulus | 47.5 | 50 | 10.5 | 2.62 | 3.48 | 4.27E−11 | 1.12E−10 | 3.80E−09 |
| GO:0050794 | regulation of cellular process | 516 | 51 | 9.9 | 2.46 | 3.24 | 2.72E−10 | 6.93E−10 | 2.43E−08 |
| GO:0050789 | regulation of biological process | 541 | 51 | 9.4 | 2.35 | 3.05 | 1.53E−09 | 3.78E−09 | 1.36E−07 |
| GO:0065007 | biological regulation | 564 | 51 | 9 | 2.25 | 2.9 | 6.70E−09 | 1.61E−08 | 5.96E−07 |
| GO:0006468 | protein phosphorylation | 109 | 10 | 9.2 | 2.29 | 2.5 | 0.0114981 | 0.02692976 | 1 |

Figure 4D:
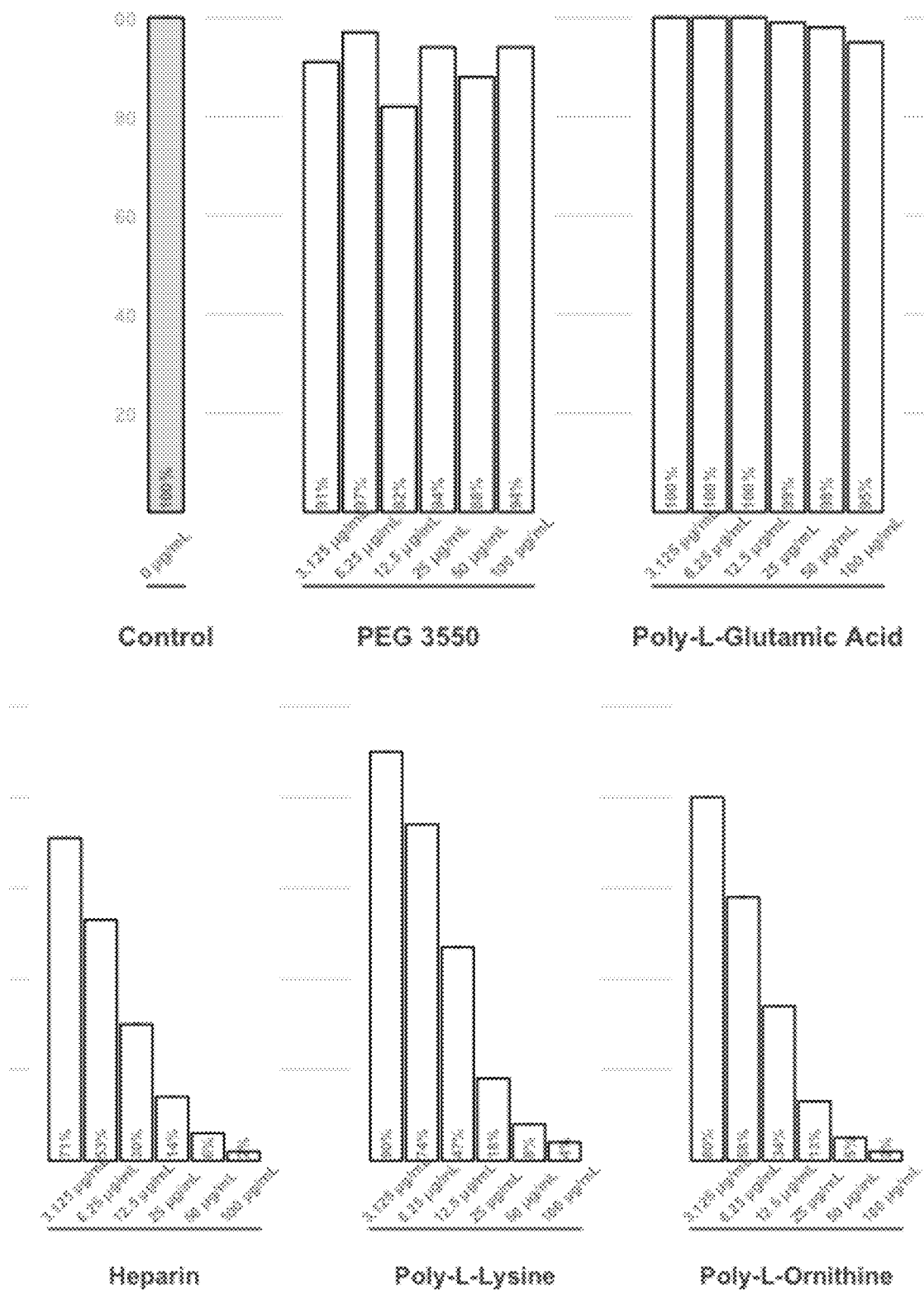

Calculated isoelectric points for both groups are high, on average, and do not differ significantly from each other or *P. falciparum* proteins (see e.g., FIG. 17). This feature seems to be conserved to exported proteins of all *Plasmodium* species and certain parasitic species of Microsporidia (see e.g., FIG. 18). The lack of *P. falciparum* taxis during invasion of host cells, alterations in cytoadhesive properties of infected erythrocytes and previously shown invasion-blocking effects of heparin prompted testing whether poly-lysine repeats in *P. falciparum* membrane proteins contribute to the overall efficiency of parasite invasion of host erythrocytes. Incubation of parasites with equal concentrations of short poly-(L) lysine or poly-(L) ornithine repeats in the media for 72 hours resulted in the efficient reduction of parasite growth for both poly-basic compounds (see e.g., FIG. 4D). The range of the effect for both polymers was similar to previously reported inhibitory effects of heparin on *P. falciparum* invasion of human erythrocytes, which served as an experimental control. Addition of poly-glutamate or poly-ethylene glycol did not affect the growth of parasites; providing evidence that that poly-basic polymers and heparin are explicitly inhibiting parasite growth. These data demonstrate that addition of poly-lysine exogenously to human erythrocyte cultures can prevent parasite growth in erythrocytes; possibly through competition with endogenously expressed poly-lysine and other polybasic proteins.

The data presented herein indicate that the *P. falciparum* translational machinery permits the translation of polyA tracks without mRNA degradation, protein attenuation, nor activation of translational surveillance pathways. It is apparent that the accommodation of polyA tracks and poly-lysine repeats in translation required multiple adaptations to be vital, and typically highly conserved components of the translational and mRNA surveillance pathways; demonstrated here. While adaptations to polyA tracks have shaped translational accuracy and efficiency of *P. falciparum* ribosomes, it is indicative that ribosome exit channel differences might be adaptations to poly-lysine and other poly-basic sequences in *Plasmodium*, based on data from other organisms. Changes in the mRNA surveillance cellular components and mechanism might have followed ribosomal adaptations. However, increase in polyA tracks in DNA and mRNA sequences could have been driven by different selective pressure than the establishment of poly-lysine repeats in proteins. Advantages of parasites to synthesize proteins with poly-lysine repeats could be solely driven by benefits in the adhesion and invasion of host cells. Enrichment of proteins with poly-lysine or poly-basic repeats at the *P. falciparum* merozoite membrane is necessary to make initial adhesion of inert parasite cells to the erythrocyte membrane and increase the efficiency of invasion. Also, it was suggested that an expansion of lysine-rich repeats in *Plasmodium* is associated with increased protein targeting to the erythrocyte periphery as seen with other poly-basic peptides. However, the conservation of both polyA tracks and poly-lysine repeats within *Plasmodium* species provides evidence against the possibility that these sequences are just signals for plasma membrane localization and cell-surface retention. It is also possible that poly-lysine repeats in proteins expressed on the surface of infected erythrocytes contribute to previously observed sequestration of infected erythrocytes in particular organs of the human. The data presented herein regarding the suppression of parasitic growth using exogenous poly-basic peptides indicate that such peptides could potentially be used as new antimalarial drugs. Further insights into differences between components of translational machinery and mRNA surveillance pathways present in *P. falciparum* and host organisms, will provide additional new drug targets against malaria. Polymers were obtained from Sigma Aldrich or Alamanda Polymers.

References

1. N. Gerald, B. Mahajan, S. Kumar, Mitosis in the human malaria parasite *Plasmodium falciparum*. *Eukaryot Cell* 10, 474-482 (2011).
2. X. M. Lu et al., Nascent RNA sequencing reveals mechanisms of gene regulation in the human malaria parasite *Plasmodium falciparum*. *Nucleic Acids Res* 45, 7825-7840 (2017).
3. F. Caro, V. Ahyong, M. Betegon, J. L. DeRisi, Genome-wide regulatory dynamics of translation in the *Plasmodium falciparum* asexual blood stages. *Elife* 3, (2014).
4. M. Zhang et al., Uncovering the essential genes of the human malaria parasite. *Science* 360, (2018).

5. G. Glockner, A. Rosenthal, K. Valentin, The structure and gene repertoire of an ancient red algal plastid genome. *J Mol Evol* 51, 382-390 (2000).
6. M. J. Gardner et al., Genome sequence of the human malaria parasite *Plasmodium falciparum*. *Nature* 419, 498-511 (2002).
7. K. Szafranski, R. Lehmann, G. Parra, R. Guigo, G. Glockner, Gene organization features in A/T-rich organisms. *J Mol Evol* 60, 90-98 (2005).
8. S. Ito-Harashima, K. Kuroha, T. Tatematsu, T. Inada, Translation of the poly(A) tail plays crucial roles in nonstop mRNA surveillance via translation repression and protein destabilization by proteasome in yeast. *Genes Dev* 21, 519-524 (2007).
9. L. Arthur et al., Translational control by lysine-encoding A-rich sequences. *Sci Adv* 1, (2015).
10. L. L. Arthur et al., Rapid generation of hypomorphic mutations. *Nat Commun* 8, 14112 (2017).
11. L. L. Arthur, S. Djuranovic, PolyA tracks, polybasic peptides, poly-translational hurdles. *Wiley Interdiscip Rev RNA*, e1486 (2018).
12. K. S. Koutmou et al., Ribosomes slide on lysine-encoding homopolymeric A stretches. *Elife* 4, (2015).
13. A. Garzia et al., The E3 ubiquitin ligase and RNA-binding protein ZNF598 orchestrates ribosome quality control of premature polyadenylated mRNAs. *Nat Commun* 8,16056 (2017).
14. S. Juszkiewicz, R. S. Hegde, Initiation of Quality Control during Poly(A) Translation Requires Site-Specific Ribosome Ubiquitination. *Mol Cell* 65, 743-750.e744 (2017).
15. E. Sundaramoorthy et al., ZNF598 and RACK1 Regulate Mammalian Ribosome-Associated Quality Control Function by Mediating Regulatory 40S Ribosomal Ubiquitylation. *Mol Cell* 65, 751-760.e754 (2017).
16. A. Saul, D. Battistutta, Codon usage in *Plasmodium falciparum*. *Mol Biochem Parasitol* 27, 35-42 (1988).
17. R. M. Coulson, N. Hall, C. A. Ouzounis, Comparative genomics of transcriptional control in the human malaria parasite *Plasmodium falciparum*. *Genome Res* 14,1548-1554 (2004).
18. E. M. Bunnik et al., Polysome profiling reveals translational control of gene expression in the human malaria parasite *Plasmodium falciparum*. *Genome Biol* 14, R128 (2013).
19. Habich M, PATACSDB—The database of polyA translational attenuators in coding sequences. *PeerJ Computer Science* 2: e45 https://doi.org/10.7717/peerj-cs.45, (2016).
20. R. J. Andrews, L. Baber, W. N. Moss, RNAStructuromeDB: A genome-wide database for RNA structural inference. *Sci Rep* 7, 17269 (2017).
21. A. M. Michel et al., GWIPS-viz: development of a ribo-seq genome browser. *Nucleic Acids Res* 42, D859-864 (2014).
22. N. T. Ingolia et al., Ribosome profiling reveals pervasive translation outside of annotated protein-coding genes. *Cell Rep* 8, 1365-1379 (2014).
23. J. L. Guler et al., Asexual populations of the human malaria parasite, *Plasmodium falciparum*, use a two-step genomic strategy to acquire accurate, beneficial DNA amplifications. *PLoS Pathog* 9, e1003375 (2013).
24. T. Tsuboi et al., Dom34:hbs1 plays a general role in quality-control systems by dissociation of a stalled ribosome at the 3' end of aberrant mRNA. *Mol Cell* 46, 518-529 (2012).
25. N. R. Guydosh, R. Green, Translation of poly(A) tails leads to precise mRNA cleavage. *RNA* 23, 749-761 (2017).
26. K. Sorber, M. T. Dimon, J. L. DeRisi, RNA-Seq analysis of splicing in *Plasmodium falciparum* uncovers new splice junctions, alternative splicing and splicing of antisense transcripts. *Nucleic Acids Res* 39, 3820-3835 (2011).
27. M. Ghorbal et al., Genome editing in the human malaria parasite *Plasmodium falciparum* using the CRISPR-Cas9 system. *Nat Biotechnol* 32, 819-821 (2014).
28. A. S. Nasamu et al., Plasmepsins IX and X are essential and druggable mediators of malaria parasite egress and invasion. *Science* 358, 518-522 (2017).
29. A. Bhattacharya, K. B. McIntosh, I. M. Willis, J. R. Warner, Why Dom34 stimulates growth of cells with defects of 40S ribosomal subunit biosynthesis. *Mol Cell Biol* 30, 5562-5571 (2010).
30. M. K. Doma, R. Parker, Endonucleolytic cleavage of eukaryotic mRNAs with stalls in translation elongation. *Nature* 440, 561-564 (2006).
31. S. E. Babbitt et al., *Plasmodium falciparum* responds to amino acid starvation by entering into a hibernatory state. *Proc Natl Acad Sci USA* 109, E3278-3287 (2012).
32. W. Wong et al., Cryo-EM structure of the *Plasmodium falciparum* 80S ribosome bound to the anti-protozoan drug emetine. *Elife* 3, (2014).
33. M. Sun et al., Dynamical features of the *Plasmodium falciparum* ribosome during translation. *Nucleic Acids Res* 43, 10515-10524 (2015).
34. Y. Matsuo et al., Ubiquitination of stalled ribosome triggers ribosome-associated quality control. *Nat Commun* 8, 159 (2017).
35. K. Kuroha et al., Receptor for activated C kinase 1 stimulates nascent polypeptide-dependent translation arrest. *EMBO Rep* 11, 956-961 (2010).
36. A. S. Wolf, E. J. Grayhack, Asc1, homolog of human RACK1, prevents frameshifting in yeast by ribosomes stalled at CGA codon repeats. *RNA* 21, 935-945 (2015).
37. H. Fujita, M. Yamagishi, Y. Kida, M. Sakaguchi, Positive charges on the translocating polypeptide chain arrest movement through the translocon. *J Cell Sci* 124, 4184-4193 (2011).
38. W. L. Hamilton et al., Extreme mutation bias and high AT content in *Plasmodium falciparum*. *Nucleic Acids Res* 45, 1889-1901 (2017).
39. L. Bannister, G. Mitchell, The ins, outs and roundabouts of malaria. *Trends Parasitol* 19, 209-213 (2003).
40. M. J. Boyle, J. S. Richards, P. R. Gilson, W. Chai, J. G. Beeson, Interactions with heparin-like molecules during erythrocyte invasion by *Plasmodium falciparum* merozoites. *Blood* 115, 4559-4568 (2010).
41. O. Brandman et al., A ribosome-bound quality control complex triggers degradation of nascent peptides and signals translation stress. *Cell* 151, 1042-1054 (2012).
42. W. H. Lang, G. Calloni, R. M. Vabulas, Polylysine is a Proteostasis Network-Engaging Structural Determinant. *J Proteome Res* 17, 1967-1977 (2018).
43. K. Kobayashi et al., Analyses of interactions between heparin and the apical surface proteins of *Plasmodium falciparum*. *Sci Rep* 3, 3178 (2013).
44. A. M. Leitgeb et al., Low anticoagulant heparin disrupts *Plasmodium falciparum* rosettes in fresh clinical isolates. *Am J Trop Med Hyg* 84, 390-396 (2011).
45. H. M. Davies, K. Thalassinos, A. R. Osborne, Expansion of Lysine-rich Repeats in *Plasmodium* Proteins Generates Novel Localization Sequences That Target the Periphery of the Host Erythrocyte. *J Biol Chem* 291, 26188-26207 (2016).
46. L. C. Romero, T. V. Nguyen, B. Deville, O. Ogunjumo, A. A. James, The MB2 gene family of *Plasmodium* species has a unique combination of S1 and GTP-binding domains. *BMC Bioinformatics* 5, 83 (2004).
47. J. F. Hancock, H. Paterson, C. J. Marshall, A polybasic domain or palmitoylation is required in addition to the CAAX motif to localize p21 ras to the plasma membrane. *Cell* 63, 133-139 (1990).

Example 2: Use of Polybasic Peptides and Polymers as Antimalarial Drugs

The following example describes studies of polybasic peptides and polymers and their uses as antimalarial agents.

Studies of binding of FITC-labeled poly-lysine to infected erythrocytes, *P. falciparum* merozoites were performed and demonstrated fast binding kinetics (order of 1-3 minutes) (see e.g., FIG. 19). Here, the parasite samples were labeled with poly-lysine-FITC. The protocol is: 200 µl of 5% hematocrite culture was spun down at 500×g for 5 min at room temperature (RT). The samples were washed 2 times with 500 µl PBS, and incubated with 500 µl labeled poly-lysine-FITC, at room temperature for 1-3 min. The samples were than washed, 3× with PBS. The pellets were resuspended in 50 µl PBS and 5 µl was loaded on a clean slide. The cover slip was sealed and immediately used for fluorescent microscopy (WUCCI). The sample procedure was done for the control sample, where cells were incubated only with the FITC solution.

It was discovered that poly-L-lysine and poly-L-ornithine do not detectably bind to other human cells (uninfected human cells) (see e.g., FIG. 20). Here, the same procedure as for above (FIG. 19) was performed for the cell culture, except for the incubation volume was 1 ml in PBS and the images were taken on a lab microscope.

$IC_{50}$ values were determined for polybasic peptides. The $IC_{50}$ values for the peptides were shown to be better than heparin ($IC_{50}$ reduced when compared to heparin) (see e.g., FIG. 21). $IC_{50}$ values were determined for various polybasic peptide lengths (10 (SEQ ID NO: 4), 20 (SEQ ID NO: 3), 30 (SEQ ID NO: 2), and 50 (SEQ ID NO: 1)). Shorter runs of polybasic peptides were shown to be less potent (10-L-lysines (SEQ ID NO: 4) and less have no activity) (see e.g., FIG. 22).

Poly-lysine was PEGylated. It was determined that PEGylation of poly-Lys generally increases stability of peptides (see e.g., FIG. 23). Poly-L-lysine of length 50 (SEQ ID NO: 1) bloodstream half-life was determined to be 30 min. PEGylated-pLys half-life was up to 14 h in rats. It was surprising that poly-ε-L-lysine was not shown to be effective against malaria.

Several malaria causing parasites have increased lysine repeats. As such, it would be expected that poly-L-lysine should target multiple targets and different types of Malaria parasites (see e.g., FIG. 24).

Intraperitoneal treatment of mice results in the reduction of parasitemia over 2 days (see e.g., FIG. 25). Treatment of mice infected with mCherry labelled *P. berghei* with 4 doses of poly-lysine peptides or PEGylated poly-lysine polymers reduces parasitemia over 7 days of infection (see e.g., FIG. 25).

For FIG. 21-FIG. 25, the general procedure for the drug assays included a total sample volume of 200 µl, every concentration was performed in triplicate, hematocrit was 2%, and starting parasitemia was 1%. The starting concentration of drug was 100 µg/ml and the serial dilution was made from the starting concentration. The end concentration was 0.39 µg/ml). The control represents growth of the parasite culture without added drug. All samples were subjected to Acridine orange staining and the FACS analysis was done on 96 well plates. FlowJo was used to calculate parasitemia.

Dose-response experiments were performed in triplicate with mixed culture of *P. falciparum* (1.0%-1.2% starting parasitemia). Parasitemias (percentage of total erythrocytes infected with parasites) were measured approximately 72 hours post compound addition by nucleic acid staining of infected red blood cells with 0.8 mg/ml acridine orange in PBS. Inhibition data were fit to a sigmoidal dose-response curve was done using Graphpad Prism 5.0.

Polylysine polymers, PEG-polylysine, and polyglutamate were obtained from Sigma Aldrich or Alamanda Polymers. Poly (L) lysine in various average molecular weights or sizes were obtained from Sigma Aldrich. Poly (L) lysine of 10 (SEQ ID NO: 4), 20 (SEQ ID NO: 3), 30 (SEQ ID NO: 2), and 50 (SEQ ID NO: 1) residues in length were obtained from Alamanda polymers. PEGylated poly (L) lysine was obtained from Alamanda Polymers.

What is claimed is:

1. A method of suppressing *Plasmodium* parasite growth or infectivity in a subject in need thereof, the method comprising:
    administering to the subject a therapeutically effective amount of a composition consisting of a biologically active polybasic antimalarial agent to target a *Plasmodium* parasite-infected cell in an amount sufficient to suppress the *Plasmodium* parasite growth or infectivity;
    wherein the biologically active polybasic antimalarial agent is poly-ornithine; and
    wherein the biologically active polybasic antimalarial agent does not include epsilon poly-lysine.

2. The method of claim 1, wherein the therapeutically effective amount of the biologically active polybasic antimalarial agent is an amount sufficient to inhibit cellular adhesion of the *Plasmodium* parasite or inhibit interaction of the *Plasmodium* parasite with an erythrocyte.

3. The method of claim 1, wherein the biologically active polybasic antimalarial agent has a net positive charge.

4. The method of claim 1, wherein the subject is a human or a mosquito.

5. The method of claim 1, wherein the subject has malaria, is suspected of having malaria, or is at risk for contracting malaria.

6. The method of claim 1, wherein the biologically active polybasic antimalarial agent:
    has a molecular weight between 1 kDa and 15 kDa or has a distribution of molecular weights having an average molecular weight between 1 kDa and 15 kDa;
    is greater than 10 polybasic amino acids or between 10 polybasic amino acids and 50 amino acids; or
    is greater than 50 polybasic amino acids.

7. The method of claim 1, wherein the *Plasmodium* parasite is selected from the group consisting of *Plasmodium falciparum, Plasmodium yoelii, Plasmodium knowlesi, Plasmodium vivax, Plasmodium berghei, Plasmodium chabaudi,* and *Plasmodium cynomolgi*.

8. The method of claim 1, wherein the biologically active polybasic antimalarial agent blocks *Plasmodium* adhesion to cells.

9. The method of claim 1, wherein the biologically active polybasic antimalarial agent substantially targets malaria parasite-infected erythrocytes and does not detectably bind to uninfected cells.

10. A method of treating malaria in a subject, the method comprising:

administering to the subject a therapeutically effective amount of a composition consisting of a biologically active polybasic antimalarial agent conjugated to a polyethylene glycol (PEG), a dextran, a rhodamine dextran, or a dendrimer, wherein the biologically active polybasic antimalarial agent is poly-ornithine; and wherein the biologically active polybasic antimalarial agent does not include epsilon poly-lysine.

11. The method of claim 10, wherein the therapeutically effective amount of the biologically active polybasic antimalarial agent is an amount sufficient to inhibit cellular adhesion of a *Plasmodium* parasite or inhibit interaction of the *Plasmodium* parasite with an erythrocyte.

12. The method of claim 10, wherein the biologically active polybasic antimalarial agent has a net positive charge.

13. The method of claim 10, wherein the subject is a human or a mosquito.

14. The method of claim 10, wherein the subject has malaria, is suspected of having malaria, or is at risk for contracting malaria.

15. The method of claim 10, wherein the biologically active polybasic antimalarial agent:

has a molecular weight between 1 kDa and 15 kDa or has a distribution of molecular weights having an average molecular weight between 1 kDa and 15 kDa;

is greater than 10 polybasic amino acids or between 10 polybasic amino acids and 50 amino acids; or is greater than 50 polybasic amino acids.

16. The method of claim 11, wherein the *Plasmodium* parasite is selected from the group consisting of *Plasmodium falciparum, Plasmodium yoelii, Plasmodium knowlesi, Plasmodium vivax, Plasmodium berghei, Plasmodium chabaudi,* and *Plasmodium cynomolgi.*

17. The method of claim 10, wherein the biologically active polybasic antimalarial agent competes with endogenous poly-lysine and polybasic proteins for cell binding or the biologically active polybasic antimalarial agent blocks *Plasmodium* adhesion to cells.

* * * * *

UNITED STATES PATENT AND TRADEMARK OFFICE
CERTIFICATE OF CORRECTION

| | | |
|---|---|---|
| PATENT NO. | : 12,274,731 B1 | Page 1 of 1 |
| APPLICATION NO. | : 16/509812 | |
| DATED | : April 15, 2025 | |
| INVENTOR(S) | : Sergej Djuranovic, Slavica Pavlovic Djuranovic and Jessey Lee Erath | |

It is certified that error appears in the above-identified patent and that said Letters Patent is hereby corrected as shown below:

In the Specification

Government Support Paragraph at Column 1, Line 14 should read:
This invention was made with government support under GM136823 awarded by the National Institutes of Health. The government has certain rights in the invention.

Signed and Sealed this
Ninth Day of September, 2025

Coke Morgan Stewart
*Acting Director of the United States Patent and Trademark Office*

SEQUENCE LISTING

```
<160> NUMBER OF SEQ ID NOS: 4

<210> SEQ ID NO 1
<211> LENGTH: 50
<212> TYPE: PRT
<213> ORGANISM: Artificial Sequence
<220> FEATURE:
<223> OTHER INFORMATION: Synthetic polybasic peptide

<400> SEQUENCE: 1

Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys Lys
                20                  25                  30

Lys Lys Lys Lys Lys Lys Lys Lys Lys Lys Lys Lys Lys Lys Lys
```

```
                        35                  40                  45
Lys Lys
    50

<210> SEQ ID NO 2
<211> LENGTH: 30
<212> TYPE: PRT
<213> ORGANISM: Artificial Sequence
<220> FEATURE:
<223> OTHER INFORMATION: Synthetic polybasic peptide

<400> SEQUENCE: 2

Lys Lys Lys Lys Lys Lys Lys Lys Lys Lys Lys Lys Lys Lys Lys Lys
1               5                   10                  15

Lys Lys Lys Lys Lys Lys Lys Lys Lys Lys Lys Lys Lys Lys
            20                  25                  30

<210> SEQ ID NO 3
<211> LENGTH: 20
<212> TYPE: PRT
<213> ORGANISM: Artificial Sequence
<220> FEATURE:
<223> OTHER INFORMATION: Synthetic polybasic peptide

<400> SEQUENCE: 3

Lys Lys Lys Lys Lys Lys Lys Lys Lys Lys Lys Lys Lys Lys Lys Lys
1               5                   10                  15

Lys Lys Lys Lys
            20

<210> SEQ ID NO 4
<211> LENGTH: 10
<212> TYPE: PRT
<213> ORGANISM: Artificial Sequence
<220> FEATURE:
<223> OTHER INFORMATION: Synthetic polybasic peptide

<400> SEQUENCE: 4

Lys Lys Lys Lys Lys Lys Lys Lys Lys Lys
1               5                   10
```